(12) United States Patent
Garthwaite et al.

(10) Patent No.: US 7,790,761 B2
(45) Date of Patent: Sep. 7, 2010

(54) BLOCKADE OF VOLTAGE DEPENDENT SODIUM CHANNELS

(75) Inventors: Giti Garthwaite, London (GB); David Selwood, London (GB); Marcel Kling, London (GB); Grant Wishart, London (GB)

(73) Assignee: University College London, London (GB)

( * ) Notice: Subject to any disclaimer, the term of this patent is extended or adjusted under 35 U.S.C. 154(b) by 1294 days.

(21) Appl. No.: 11/312,569

(22) Filed: Dec. 21, 2005

(65) Prior Publication Data

US 2006/0100248 A1     May 11, 2006

Related U.S. Application Data

(62) Division of application No. 10/203,001, filed as application No. PCT/GB01/00472 on Feb. 5, 2001, now Pat. No. 7,009,056.

(30) Foreign Application Priority Data

Feb. 4, 2000    (GB) .................................. 0002666.6

(51) Int. Cl.
    *A61K 31/41* (2006.01)
    *A61K 31/4196* (2006.01)
    *A61K 31/4166* (2006.01)

(52) U.S. Cl. ...................... 514/383; 514/403; 514/406

(58) Field of Classification Search ................ 514/403, 514/406, 383
    See application file for complete search history.

(56) References Cited

U.S. PATENT DOCUMENTS 5,462,960 A * 10/1995 Barth et al. ................. 514/406

| 5,795,965 | A | 8/1998 | Tsuchiya et al. |
| 5,877,211 | A | 3/1999 | Woodward |
| 5,977,378 | A | 11/1999 | Muller |
| 6,509,367 | B1 | 1/2003 | Martin |

FOREIGN PATENT DOCUMENTS

| DE | 19642255 A | 4/1998 |
| DE | 19642323 A | 4/1998 |
| DE | 19834714 A | 2/2000 |
| EP | 0459887 A | 4/1991 |
| EP | 0667345 A | 8/1995 |
| WO | WO 98/43612 | 10/1998 |
| WO | WO 99/32462 | 7/1999 |
| WO | WO 99/39712 | 8/1999 |

OTHER PUBLICATIONS

Czollner, L. Arch Pharm. 1990, 323, 221.
Garthwaite et al., 1999, Neuroscience, 94, 1219-1230.
Neufeld et al., 1999, Natl. Acad. Sci. USA, 96, 9944-9948.
Stys et al., 1998, J.Cereb. Blood Flow Metab., 18, 2-25.
Taylor et al., 1995, Trends Pharmacol. Sci., 16, 309-316.
Urenjak et al., 1996, Pharmacol. Rev., 48, 21-67.
Hobbs, A.J., tlps, 1997, 18, 484.
Garthwaite et al, 1999, vol. 11, pp. 4367-4372 European J. of Neuroscience.
Maybridge Chemical Company, Cornwall, UK—catalogue 1998.

* cited by examiner

*Primary Examiner*—James O Wilson
*Assistant Examiner*—Ebenezer Sackey
(74) *Attorney, Agent, or Firm*—Nixon & Vanderhye P.C.

(57) ABSTRACT

Compounds of Formula I and pharmaceutically acceptable salts thereof, are capable of blockading voltage-dependent sodium channels and are useful in particular, in treating glaucoma and multiple sclerosis.

14 Claims, No Drawings

BLOCKADE OF VOLTAGE DEPENDENT SODIUM CHANNELS

The present application is a divisional of Ser. No. 10/203,001, filed Feb. 25, 2003 (issued as U.S. Pat. No. 7,009,056 on Mar. 7, 2006), which is a 371 U.S. national phase of PCT/GB01/00472, filed Feb. 5, 2001, which claims benefit of UK 0002666.6 filed Feb. 4, 2000, the entire contents of each of which is incorporated herein by reference.

The present invention relates to a series of pyrazole and indazole compounds capable of blockading voltage dependent sodium channels. Voltage-dependent sodium channels are found in the cell membranes of neurones (including their axons) where they are fundamental to the generation and propagation of electrical impulses. Under pathological conditions (such as ischaemia), however, sodium channels become abnormally activated resulting in an excessive flow of sodium ions into the cytoplasm. The rise in cellular sodium ions then causes a large inflow of calcium ions leading to the activation of several mechanisms that lead to irreversible loss of function and subsequent degeneration (Taylor, C. P. & Meldnim, B. S. (1995), *Trends. Pharmacol. Sci.* 16, 309-316 and Urenjak J. & Obrenovitch, T. P. (1996), *Pharmacol. Rev.* 48, 21-67).

It has already proved possible to produce pharmacological agents capable of stopping excessive activity of sodium channels without adversely affecting their normal function. Indeed, this is the principal mode of action of several widely-used and well-tolerated antiepileptic drugs (e.g. phenytoin, carbamazapine and lamotrigine). Sodium channel inhibitors have been shown to be protective towards neurones in the grey matter in several models of cerebral ischaemia (Taylor, C. P. & Meldrum, B. S. (1995), *Trends. Pharmacol. Sci.* 16, 309-316 and Urenjak J. & Obrenovitch, T. P. (1996), *Pharmacol. Rev.* 48, 21-67). More recently, it has become evident that certain sodium channel inhibitors are highly effective in protecting axons in the in vitro optic nerve from irreversible damage imposed by severe deprivation of oxygen and glucose (Stys, P. K. (1998), *J. Cereb. Blood Flow Metab* 18, 2-25 & Garthwaite et al (1999), *Neuroscience,* 94, 1219-1230).

It has now, surprisingly, been found that a series of specific pyrazole and indazole compounds are capable of inhibiting voltage dependent sodium channels. They can achieve a highly effective protective action on white matter, or myelin coated nerve cell fibres. Such a neuroprotective effect on ganglion cells and axons can lead to valuable therapeutic benefits.

Certain pyrazoles and indazoles are known per se. Thus, 3-(5'-hydroxymethyl-2'-furyl)-1-benzylindazole (YC-1) is known as an activator of soluble guanylate cyclase (Hobbs, A. J., TIPS, December 1997, Vol 18, p.484). Further, EP-A-667345 discloses a number of indazole analogues of YC-1 as inhibitors of platelet aggregation.

DE-A-19642323 discloses a number of 1-benzyl-indazole compounds for use in treating circulation disorders and DE-A-19642255 discloses similar compounds for use as vasodilators.

The present invention provides the use of a compound of the formula (I), or a pharmaceutically acceptable salt thereof in the manufacture of a medicament for use in blockading voltage-dependent sodium channels

wherein:
$R_1$ is hydrogen, $C_1$-$C_6$ alkyl, aryl or —($C_1$-$C_6$ alkyl)-aryl;
$R_2$ is aryl, heteroaryl, 3- to 6-membered heterocyclyl, $C_3$-$C_6$ carbocyclyl or —XR wherein X is a divalent $C_1$-$C_6$ alkyl, $C_2$-$C_6$ alkenyl or $C_2$-$C_6$ alynyl group and R is aryl, heteroaryl, 3- to 6-membered heterocyclyl or $C_3$-$C_6$ carbocyclyl, or $R_2$ is $C_1$-$C_6$ alkyl, $C_2$-$C_6$ alkenyl, $C_2$-$C_6$ alkynyl or —COR, —CONR'R" or —$CO_2$R' wherein each R' and R" is the same or different and is selected from hydrogen, $C_1$-$C_6$ alkyl, aryl and heteroaryl and R is selected from $C_1$-$C_6$ alkyl, aryl and heteroaryl; and
either $R_3$ and $R_4$, together with the carbon atoms to which they are attached, form a phenyl group, or $R_3$ and $R_4$ are the same or different and are selected from hydrogen, $C_1$-$C_6$ alkyl, $C_2$-$C_6$ alkenyl, $C_2$-$C_6$ alkynyl, aryl, heteroaryl 3- to 6-membered heterocyclyl, —COR, —CONR'—NR"COR, —CONR'—NR"CS—R, —$CO_2$R', —CONR'—NR"—$CO_2$R', —CONR'—NR"—CS—OR', —CONR'R, —CONR'—NR"CO—NR'"R"" and —CONR'—NR"CS—NR'"R"", wherein each R is the same or different and is selected from $C_1$-$C_6$ alkyl aryl, $C_1$-$C_6$ alkyl)aryl and heteroaryl and each R', R", R'" and R"" is the same or different and is selected from hydrogen, $C_1$-$C_6$ alkyl aryl, -($C_1$-$C_6$ alkyl)-aryl and heteroaryl.

Typically,
$R_1$ is hydrogen, $C_1$-$C_6$ alkyl, aryl or —($C_1$-$C_6$ alkyl)-aryl;
$R_2$ is aryl, heteroaryl, 3- to 6-membered heterocyclyl, $C_3$-$C_6$ carbocyclyl or —XR wherein X is a divalent $C_1$-$C_6$ alkyl, $C_2$-$C_6$ alkenyl or $C_2$-$C_6$ alkynyl group and R is aryl, heteroaryl, 3- to 6-membered heterocyclyl or $C_3$-$C_6$ carbocyclyl, or $R_2$ is $C_1$-$C_6$ alkyl, $C_2$-$C_6$ alkenyl, $C_2$-$C_6$ alkynyl or —COR, —CONR'R" or —$CO_2$R' wherein each R' and R" is the same or different and is selected from hydrogen, $C_1$-$C_6$ alkyl and aryl and R is selected from $C_1$-$C_6$ alkyl or aryl; and
either $R_3$ and $R_4$, together with the carbon atoms to which they are attached, form a phenyl group, or $R_3$ and $R_4$ are the same or different and are selected from hydrogen, $C_1$-$C_6$ alkyl, $C_2$-$C_6$ alkenyl, $C_2$-$C_6$ alkynyl, aryl, heteroaryl, 3- to 6-membered heterocyclyl, —COR, —CONR'—NR"COR, —CONR'—NR"CS—R, —$CO_2$R', —CONR'—NR"—$CO_2$R', —CONR'—NR"—CS—OR', —CONR'R", —CONR'—NR"CO—NR'"R"" and —CONR'—N"CS—NR'"R"", wherein each R is the same or different and is selected from $C_1$-$C_6$ alkyl and aryl and each R', R", R'" and R"" is the same or different and is selected from hydrogen, $C_1$-$C_6$ alkyl and aryl.

As used herein, a $C_1$-$C_6$ alkyl group or moiety is a linear or branched alkyl group or moiety. Suitable such alkyl groups and moieties include $C_1$-$C_4$ alkyl groups and moieties, for example methyl, ethyl, n-propyl, i-propyl, n-butyl and t-butyl. Methyl, ethyl, n-butyl and t-butyl are preferred.

A $C_1$-$C_6$ alkyl group or moiety can be unsubstituted or substituted at any position Typically, it is unsubstituted or carries one or two substituents. Suitable substituents include halogen, cyano, nitro, hydroxy, $C_1$-$C_6$ alkoxy, for example methoxy, and —NR'R" wherein R' and R" are the same or different and represent hydrogen or $C_1$-$C_6$ alkyl. Preferred substituents are halogen, $NMe_2$, NHEt, $NH_2$ and OMe. Further, a haloalkyl group is a preferred substituted alkyl group.

As used herein, a $C_2$-$C_6$ alkenyl group or moiety can be linear or branched. Suitable such alkenyl groups and moieties include $C_2$-$C_4$ alkenyl groups and moieties such as ethenyl, propenyl or butenyl.

A $C_2$-$C_6$ alkenyl group or moiety can be unsubstituted or substituted at any position. Typically, it is unsubstituted or carries one or two substituents. Suitable substituents include halogen, cyano, nitro, hydroxy, $C_1$-$C_6$ alkoxy, for example methoxy, and —NR'R" wherein R' and R" are the same or different and represent hydrogen or $C_1$-$C_6$ alkyl. Preferred substituents are halogen, $NMe_2$, NHEt, $NH_2$ and OMe.

As used herein, a $C_2$-$C_6$ alkynyl group or moiety can be linear or branched. Suitable such alkynyl groups and moieties include $C_3$-$C_4$ alkynyl groups and moieties such as ethynyl, propynyl and butynyl. An alkynyl group or moiety can be unsubstituted or substituted at any position. Typically, it is unsubstituted or carries one or two substituents. Suitable substituents include halogen, cyano, nitro, hydroxy, $C_1$-$C_6$ alkoxy, for example methoxy, and —NR'R" wherein R' and R" are the same or different and represent hydrogen or $C_1$-$C_6$ alkyl. Preferred substituents are halogen, $NMe_2$, NHEt, $NH_2$ and OMe.

A —($C_1$-$C_6$ alkyl)aryl group is typically a said $C_1$-$C_6$ alkyl group joined to an aryl group, as defined below. It is preferably benzyl or -ethyl-phenyl.

A halogen atom is typically a chlorine, fluorine, bromine or iodine atom. It is preferably chlorine or fluorine.

As used herein, an aryl group or moiety is typically a $C_6$-$C_{10}$ aryl group or moiety. Suitable such aryl groups and moieties include phenyl and naphthyl. Phenyl is preferred.

An aryl group or moiety may be substituted or unsubstituted at any position. Typically, it is unsubstituted or carries 1, 2, 3 or 4 substituents. Suitable substituents include halogen, hydroxyl, —SH, $C_1$-$C_6$ alkyl, for example —$CF_3$ and —$CCl_3$, $C_2$-$C_6$ alkenyl, $C_2$-$C_6$ alkynyl, aryl, heteroaryl, 3- to 6-membered heterocyclyl, $C_3$-$C_6$ carbocyclyl, —XY wherein X is a divalent $C_1$-$C_6$ alkyl, $C_1$-$C_6$ alkenyl or $C_1$-$C_6$ akyl group and Y is an aryl or heteroaryl group, nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkenylthio, —OR, —SR, —COR', —$CO_2$R", —$CONR'''R''''$, —$NR'''R''''$ and —NR"—CO—R' wherein R is aryl, heteroaryl or —XY wherein X is a divalent $C_1$-$C_6$ alkyl, $C_2$-$C_6$ alkenyl or $C_2$-$C_6$ alkynyl group and Y is an aryl or heteroaryl group, R' is selected from R, $C_1$-$C_6$ alkyl, $C_2$-$C_6$ alkenyl and $C_2$-$C_6$ alkynyl, R" is selected from R' and hydrogen and R''' and R'''' are the same or different and are selected from R', hydrogen and hydroxy. Further suitable substituents include —S—X—COR, —O—X—COR, —S—X—$CO_2$R and —O—X—$CO_2$R wherein X is a divalent $C_1$-$C_6$ alkyl, $C_2$-$C_6$ alkenyl or $C_2$-$C_6$ alkynyl group and R is $C_1$-$C_6$ alkyl, aryl or heteroaryl.

Preferred substituents include halogen, for example chlorine, fluorine and bromine, —SH, hydroxy, $C_1$-$C_6$ alkyl, for example t-butyl, methyl, —$CF_3$, —$CCl_3$, —$CH_2OH$, —$CH_2NMe_2$, —$CH_2NH_2$ and —$(CH_2)_3$OMe, aryl, heteroaryl, 3- to 6-membered heterocyclyl, $C_3$-$C_6$ carbocyclyl, —($C_1$-$C_6$ alkyl)-aryl, —($C_1$-$C_6$ alkyl)-heteroaryl, nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkynylthio, —OR, —SR, —COR', —$CO_2$R", —$CONR'''R''''$, —$NR'''R''''$ and —NR"—CO—R' wherein R is aryl or —($C_1$-$C_6$ alkyl)-aryl, R' is selected from R or $C_1$-$C_6$ alkyl R" is selected from R' and hydrogen and R''' and R'''' are the same or different and are selected from R', hydrogen and hydroxy, —S—($C_1$-$C_6$ alkyl)—CO—R and —S—($C_1$-$C_6$ alkyl)-$CO_2$R, wherein R is aryl or $C_1$-$C_6$ alkyl. Typically, these preferred substituents are selected from halogen, for example chlorine, fluorine and bromine, —SH, hydroxy, $C_1$-$C_6$ alkyl, for example t-butyl, methyl, —$CF_3$, —$CCl_3$, —$CH_2OH$, —$CH_2NMe_2$, —$CH_2NH_2$ and —$(CH_2)_3$OMe, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_1$-$C_6$ alkylthio, $C_2$-$C_6$ alkenylthio, —OR, —SR, —COR', —$CO_2$R", —$CONR'''R''''$ and —$NR'''R''''$ wherein R is aryl or —($C_1$-$C_6$ alkyl)-aryl, R' is selected from R or $C_1$-$C_6$ alkyl, R" is selected from R' and hydrogen and R''' and R'''' are the same or different and are selected from R', hydrogen and hydroxy, and —S—($C_1$-$C_6$ alkyl)-CO—R, wherein R is aryl or $C_1$-$C_6$ alkyl.

More preferred substituents include halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2OH$, —$CH_2NMe_2$, —$CH_2NH_2$ and —$(CH_2)_3$ OMe, aryl, for example phenyl, heteroaryl, for example oxazolyl and pyridyl, $C_3$-$C_6$ carbocyclyl, for example cyclohexane, —($C_1$-$C_6$ alkyl)-aryl, for example —$CH_2$-(4-methoxyphenyl), —$C_1$-$C_6$ alkoxy, $C_2$-$C_6$ alkenyloxy, $C_2$-$C_6$ alkynyloxy, $C_1$-$C_6$ alkylthio, for example methylthio and ethylthio, $C_2$-$C_6$ alkenylthio, for example ethenylthio and propenylthio, $C_2$-$C_6$ alkypylthio, for example propynylthio, —O-aryl, for example —O-phenyl, —O—($C_1$-$C_6$ alkyl)aryl, for example —O—($CH_2$)-phenyl, —$CO_2$H, —$CO_2$—($C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$_2$NMe$_2$, —CON(OH)—($C_1$-$C_6$ alkyl)aryl, for example —CON(OH)—$CH_2$-phenyl, NR'R" wherein R' and R" are the same or different and are hydrogen or $C_1$-$C_6$ alkyl, for example $NH_2$, $NMe_2$ and NHEt, —NH—CO—($C_1$-$C_6$ alkyl), for example —NH—CO—Me, —S—($C_1$-$C_6$ alkyl)-aryl for example —S—$CH_2$-phenyl, —S—($C_1$-$C_6$ alkyl)-CO—R and —S—($C_1$-$C_6$ alkyl)-$CO_2$R wherein R is aryl, for example phenyl, or $C_1$-$C_6$ alkyl, for example ethyl or t-butyl. Typically, these more preferred substituents are selected from halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2OH$, —$CH_2NMe_2$, —$CH_2NH_2$ and —$(CH_3)_3$ OMe, aryl, for example phenyl, $C_3$-$C_6$ carbocyclyl, for example cyclohexane, $C_1$-$C_6$ alkoxy, $C_2$-$C_6$ alkenyloxy, $C_1$-$C_6$ alkylthio, for example methylthio and ethylthio, $C_2$-$C_6$ alkenylthio, for example ethenylthio and propenylthio, —$CO_2$H, —$CO_2$—($C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$_2$NMe$_2$, —CON(OH)—($C_1$-$C_6$ alkyl)-aryl, for example —CON(OH)—$CH_2$-phenyl, NR'R" wherein R' and R" are the same or different and are hydrogen or $C_1$-$C_6$ alkyl, for example $NH_2$, $NMe_2$ and NHEt, —S—($C_1$-$C_6$ alkyl)aryl for example —S—$CH_2$-phenyl, and —S—($C_1$-$C_6$ alkyl)-CO—R wherein R is aryl, for example phenyl, or $C_1$-$C_6$ alkyl, for example ethyl or t-butyl.

Particularly preferred substituents are halogen, for example chlorine, fluorine and bromine, $C_1$-$C_6$ alkyl, for example —$CF_3$, methyl and t-butyl, $C_1$-$C_6$ alkoxy, for example methoxy, aryl, for example phenyl, heteroaryl, for example oxazolyl and pyridyl, $C_3$-$C_6$ cycloalkyl, for example cyclohexane, aryloxy, for example phenyloxy, —($C_1$-$C_6$ alkyl)-aryl, for example —$CH_2$-(4-methoxyphenyl), —O—($C_1$-$C_6$ alkyl)-aryl, for example benzyloxy, —$NMe_2$, —CONH-aryl, for example —CONH-phenyl, and —NH—CO($C_1$-$C_6$ alkyl), for example —NH—CO-Me. Typically, these particularly preferred substituents are selected from halogen, for example chlorine, fluorine and bromine, $C_1$-$C_6$ alkyl, for example —$CF_3$, methyl and t-butyl, aryl, for example phenyl, and $C_3$-$C_6$ cycloalkyl, for example cyclohexane.

An aryl group or moiety may optionally be fused to a further said aryl group or moiety or to a carbocyclic, heterocyclic or heteroaryl group or moiety.

As used herein, a carbocyclic group or moiety is a non-aromatic, saturated or unsaturated hydrocarbon ring having from 3 to 6 carbon atoms. Preferably it is a saturated hydrocarbon ring (i.e. a cycloalkyl group) having from 3 to 6 carbon atoms. Examples include cyclopropyl, cyclobutyl, cyclopentyl and cyclohexyl. It is preferably cyclohexyl.

A carbocyclic group may be unsubstituted or substituted at any position. Typically, it is unsubstituted or carries up to 3 substituents. Suitable substituents include halogen, hydroxyl, —SH, $C_1$-$C_6$ alkyl, for example —$CF_3$ and —$CCl_3$, $C_2$-$C_6$ alkenyl, $C_2$-$C_6$ alkynyl, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkynylthio, —OR, —SR, —COR', —$CO_2$R'', —CONR'''R'''' and —NR'''R'''' wherein R is aryl, heteroaryl or —XY wherein X is a divalent $C_1$-$C_6$ alkyl, $C_2$-$C_6$ alkenyl or $C_2$-$C_6$ alkynyl group and Y is an aryl or heteroaryl group, R' is selected from R, $C_1$-$C_6$ alkyl, $C_2$-$C_6$ alkenyl and $C_2$-$C_6$ alkynyl, R'' is selected from R' and hydrogen and R''' and R'''' are the same or different and are selected from R', hydrogen and hydroxy. Further suitable substituents include —S—X—COR and —O—X—COR, wherein X is a divalent $C_1$-$C_6$ alkyl, $C_2$-$C_6$ alkenyl or $C_2$-$C_6$ alkynyl group and R is aryl or heteroaryl.

Preferred substituents include halogen, for example chlorine, fluorine and bromine, —SH, hydroxy, $C_1$-$C_6$ alkyl, for example t-butyl, methyl, —$CF_3$, —$CCl_3$, —$CH_2OH$, —$CH_2NMe_2$, —$CH_2NH_2$ and —$(CH_2)_3$OMe, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_1$-$C_6$ alkylthio, $C_2$-$C_6$ alkenylthio, —OR, —SR, —COR', —$CO_2$R'', —CONR'''R'''' and —NR'''R'''' wherein R is aryl or —($C_1$-$C_6$ alkyl)-aryl, R' is selected from R or $C_1$-$C_6$ alkyl, R'' is selected from R' and hydrogen and R''' and R'''' are the same or different and are selected from R', hydrogen and hydroxy, and —S—($C_1$-$C_6$ alkyl)-CO—R, wherein R is aryl or $C_1$-$C_6$ alkyl.

More preferred substituents include halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2OH$, —$CH_2NMe_2$, —$CH_2NH_2$ and —$(CH_2)_3$OMe, aryl, for example phenyl, $C_3$-$C_6$ carbocyclyl, for example cyclohexane, $C_1$-$C_6$ alkoxy, $C_2$-$C_6$ alkenyloxy, $C_1$-$C_6$ alkylthio, for example methylthio and ethylthio, $C_2$-$C_6$ alkenylthio, for example ethenylthio and propenylthio, —$CO_2$H, —$CO_2$—($C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$_2$NMe$_2$, —CON(OH)—($C_1$-$C_6$ alkyl)-aryl, for example —CON(OH)—$CH_2$-phenyl, NR'R'' wherein R' and R'' are the same or different and are hydrogen or $C_1$-$C_6$ alkyl, for example $NH_2$, $NMe_2$ and NHEt, —S—($C_1$-$C_6$ alkyl)-aryl for example —S—$CH_2$-phenyl, and —S—($C_1$-$C_6$ alkyl)-CO—R wherein R is aryl, for example phenyl, or $C_1$-$C_6$ alkyl, for example ethyl or t-butyl.

As used herein, a heteroaryl group or moiety is typically a 5- to 10-membered aromatic ring, for example a 5- or 6-membered ring, containing at least one heteroatom selected from O, S and N. Examples include pyrrolyl, furanyl, thienyl, oxadiazolyl and triazolyl. Further examples include isoxazolyl and pyridyl. Preferred heteroaryl groups are furanyl, oxadiazolyl, isoxazolyl, pyridyl and triazolyl groups. Typically, these preferred heteroaryl groups are selected from furanyl, oxadiazolyl and triazolyl groups.

A heteroaryl group or moiety may be unsubstituted or substituted at any position. Typically, it is unsubstituted or carries 1, 2 or 3 substituents. Suitable substituents include halogen, hydroxyl, —SH, $C_1$-$C_6$ alkyl, for example —$CF_3$ and —$CCl_3$, $C_2$-$C_6$ alkenyl, $C_2$-$C_6$ alkynyl, aryl, heteroaryl, 3- to 6-membered heterocyclyl, $C_3$-$C_6$ carbocyclyl, —XY wherein X is a divalent $C_1$-$C_6$ alkyl, $C_2$-$C_6$ alkenyl or $C_2$-$C_6$ alkynyl group and Y is an aryl or heteroaryl group, nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkynylthio. —OR, —SR, —COR', —$CO_2$R'', —CONR'''R'''', —NR'''R'''' and —NR''—CO—R' wherein R is aryl, heteroaryl or —XY wherein X is a divalent $C_1$-$C_6$ alkyl, $C_2$-$C_6$ alkenyl or $C_2$-$C_6$ alkynyl group and Y is an aryl or heteroaryl group, R' is selected from R, $C_1$-$C_6$ alkyl, $C_2$-$C_6$ alkenyl and $C_2$-$C_6$ alkynyl, R'' is selected from R' and hydrogen and R''' and R'''' are the same or different and are selected from R', hydrogen and hydroxy. Further suitable substituents include —S—X—COR, —O—X—COR, —S—X—$CO_2$R and —O—X—$CO_2$R, wherein X is a divalent $C_1$-$C_6$ alkyl, $C_2$-$C_6$ alkenyl or $C_2$-$C_6$ alkynyl group and R is $C_1$-$C_6$ alkyl, aryl or heteroaryl.

Preferred substituents include halogen, for example chlorine, fluorine and bromine, —SH, hydroxy, $C_1$-$C_6$ alkyl, for example t-butyl, methyl, —$CF_3$, —$CCl_3$, —$CH_2OH$, —$CH_2NMe_2$, —$CH_2NH_2$ and —$(CH_2)_3$OMe, aryl, heteroaryl, 3- to 6-membered heterocyclyl, $C_3$-$C_6$ carbocyclyl, —($C_1$-$C_6$ alkyl)-aryl, —($C_1$-$C_6$ alkyl)-heteroaryl nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkynylthio, —OR, —SR, —COR', —$CO_2$R'', —CONR'''R'''', —NR'''R'''' and —NR''—CO—R' wherein R is aryl or —($C_1$-$C_6$ alkyl)-aryl, R' is selected from R or $C_1$-$C_6$ alkyl, R'' is selected from R' and hydrogen and R''' and R'''' are the same or different and are selected from R', hydrogen and hydroxy, —S—($C_1$-$C_6$ alkyl)-CO—R and —S—($C_1$-$C_6$ alkyl)$CO_2$—R, wherein R is aryl or $C_1$-$C_6$ alkyl. Typically, these preferred substituents are selected from halogen, for example chlorine, fluorine and bromine, —SH, hydroxy, $C_1$-$C_6$ alkyl, for example t-butyl, methyl, —$CF_3$, —$CCl_3$, —$CH_2OH$, —$CH_2NMe_2$, —$CH_2NH_2$ and —$(CH_2)_3$OMe, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_1$-$C_6$ alkylthio, $C_2$-$C_6$ alkenylthio, —OR, —SR, —COR', —$CO_2$R'', —CONR'''R'''' and —NR'''R'''' wherein R is aryl or —($C_1$-$C_6$ alkyl)-aryl, R' is selected from R or $C_1$-$C_6$ alkyl, R'' is selected from R' and hydrogen and R''' and R'''' are the same or different and are selected from R', hydrogen and hydroxy, and —S—($C_1$-$C_6$ alkyl)-CO—R, wherein R is aryl or $C_1$-$C_6$ alkyl.

More preferred substituents include halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2OH$, —$CH_2NMe_2$, —$CH_2NH_2$ and —$(CH_2)_3$OMe, aryl, for example phenyl, heteroaryl, for example oxazolyl and pyridyl, $C_3$-$C_6$ carbocyclyl, for example cyclohexane, —($C_1$-$C_6$ alkyl)-aryl, for example —$CH_2$-(4-methoxyphenyl), $C_1$-$C_6$ alkoxy, $C_2$-$C_6$ alkenyloxy, $C_2$-$C_6$ alkynyloxy, $C_1$-$C_6$ alkylthio, for example methylthio and ethylthio, $C_2$-$C_6$ alkenylthio, for example ethenylthio and propenylthio, $C_2$-$C_6$ alkynylthio, for example propynylthio, O-aryl, for example —O-phenyl, —O—($C_1$-$C_6$ alkyl)-aryl, for example —O—($CH_2$)-phenyl, —$CO_2$H, —$CO_2$—($C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$NMe_2$, —CON(OH)—($C_1$-$C_6$ alkyl)-aryl, for example —CON(OH)—$CH_2$-phenyl, NR'R" wherein R' and R" are the same or different and are hydrogen or $C_1$-$C_6$ alkyl, for example $NH_2$, $NMe_2$ and NHEt, —NH—CO—($C_1$-$C_6$ alkyl), for example —NH—CO—Me, —S—($C_1$-$C_6$ alkyl)-aryl for example —S—$CH_2$-phenyl, —S—($C_1$-$C_6$ alkyl)-CO—R and —S—($C_1$-$C_6$ alkyl)-$CO_2$—R, wherein R is aryl, for example phenyl, or $C_1$-$C_6$ alkyl, for example ethyl or t-butyl. Typically, these more preferred substituents are selected from halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2$OH, —$CH_2NMe_2$, —$CH_2NH_2$ and —($CH_2$)$_3$OMe, aryl, for example phenyl, $C_3$-$C_6$ carbocyclyl, for example cyclohexane, $C_1$-$C_6$ alkoxy, $C_2$-$C_6$alkenyloxy, $C_1$-$C_6$ alkylthio, for example methylthio and ethylthio, $C_2$-$C_6$ alkenylthio, for example ethenylthio and propenylthio, —$CO_2$H, —$CO_2$—($C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$_2NMe_2$, —CON(OH)—($C_1$-$C_6$ alkyl)-aryl, for example —CON(OH)—$CH_2$-phenyl, NR'R" wherein R' and R" are the same or different and are hydrogen or $C_1$-$C_6$ alkyl, for example $NH_2$, NMe and NHEt, —S—($C_1$-$C_6$ alkyl)-aryl for example —S—$CH_2$-phenyl, and —S—($C_1$-$C_6$ alkyl)-CO—R wherein R is aryl, for example phenyl, or $C_1$-$C_6$ alkyl, for example ethyl or t-butyl.

Particularly preferred substituents include $C_1$-$C_6$ alkyl, for example —$CH_2$OH, —$CH_2NH_2$, —($CH_2$)$_3$OMe, —$CH_2NMe_2$, t-butyl and methyl, halogen, for example chlorine, —SH, hydroxy, aryl, for example phenyl, $C_3$-$C_6$ carbocyclyl, for example cyclohexane, heteroaryl, for example oxadiazolyl and pyridyl, aryloxy, for example phenyloxy, —($C_1$-$C_6$ alkyl)-aryl, for example —$CH_2$-(4-methoxyphenyl), —O—($C_1$-$C_6$ alkyl)-aryl, for example benzyloxy, $C_1$-$C_6$ alkoxy, $C_2$-$C_6$ alkenyloxy, $C_2$-$C_6$ alkynyloxy, $C_1$-$C_6$ alkylthio, for example methylthio, $C_2$-$C_6$ alkenylthio, for example propenylthio, $C_2$-$C_6$ alkynylthio, for example propynylthio, —$NMe_2$, —NH—CO—($C_1$-$C_6$ alkyl), for example —NH—CO—Me, —$CO_2$—($C_1$-$C_6$ alkyl), for example —$CO_2$Me, —CONH-aryl, for example —CONH-phenyl, —CONHOH, —CON(OH)—($C_1$-$C_6$ alkyl)-aryl, for example —CON(OH)-benzyl, —S—($C_1$-$C_6$ alkyl)-aryl, for example —S—$CH_2$-phenyl, —S—($C_1$-$C_6$ alkyl)-CO—R wherein R is aryl or $C_1$-$C_6$ alkyl, for example —S—$CH_2$—CO-phenyl, —S—$CH_2$—CO-Et and —S—$CH_2$—CO-tBu and —S—($C_1$-$C_6$ alkyl)-$CO_2$R wherein R is aryl or $C_1$-$C_6$ alkyl, for example —S—$CH_2$—$CO_2$Et. Typically, these particularly preferred substituents are selected from $C_1$-$C_6$ alkyl, for example —$CH_2$OH, —$CH_2NH_2$, —($CH_2$)$_3$OMe, —$CH_2NMe_2$ and methyl, halogen, —SH, hydroxy, aryl, for example phenyl, $C_1$-$C_6$ alkoxy, $C_2$-$C_6$ alkenyloxy, $C_1$-$C_6$ alkylthio, for example methylthio, $C_2$-$C_6$ alkenylthio, for example propenylthio, —$CO_2$—($C_1$-$C_6$ alkyl), for example —$CO_2$Me, —CONH-aryl, for example —CONH-phenyl, —CONHOH, —CON(OH)—($C_1$-$C_6$ alkyl)-aryl, for example —CON(OH)-benzyl, —S—($C_1$-$C_6$ alkyl)-aryl, for example —S—$CH_2$-phenyl and —S—($C_1$-$C_6$ alkyl)-CO—R wherein R is aryl or $C_1$-$C_6$ alkyl, for example —S—$CH_2$—CO-phenyl, —S—$CH_2$—CO-Et and —S—$CH_2$—CO-tBu.

A heteroaryl group or moiety may optionally be fused to a said aryl group or moiety, to a further heteroaryl group or moiety or to a heterocyclic or carbocyclic group or moiety.

As used herein, a 3- to 6-membered heterocyclic group or moiety is typically a non-aromatic, saturated or unsaturated $C_3$-$C_6$ carbocyclic ring in which one or more, for example 1, 2 or 3, of the carbon atoms are replaced by a heteroatom selected from N, O and S. Saturated heterocyclic groups are preferred. Suitable 3- to 6-membered heterocyclic groups include piperidyl, piperazinyl and tetrahydrofuryl groups.

A 3- to 6-membered heterocyclic group may be unsubstituted or substituted at any position Typically, it is unsubstituted or carries 1, 2 or 3 substituents. Suitable substituents include halogen, hydroxyl, —SH, $C_1$-$C_6$ alkyl, for example —$CF_3$ and —$CCl_3$, $C_2$-$C_6$ alkenyl, $C_2$-$C_6$ alkynyl, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_2$-$C_6$ alkynyloxy, $C_1$-$C_6$ alkylthio, $C_2$-$C_6$ alkenylthio, $C_2$-$C_6$ alkylthio, —OR, —SR, —COR', —$CO_2$R", —CONR'''R"" and —NR'''R"" wherein R is aryl, heteroaryl or —XY wherein X is a divalent $C_1$-$C_6$ alkyl, $C_2$-$C_6$ alkenyl or $C_2$-$C_6$ alkynyl group and Y is an aryl or heteroaryl group, R' is selected from R, $C_1$-$C_6$ alkyl, $C_2$-$C_6$ alkenyl and $C_2$-$C_6$ alkynyl, R" is selected from R' and hydrogen and R''' and R"" are the same or different and are selected from R', hydrogen and hydroxy. Further suitable substituents include —S—X—COR and —O—X—COR, wherein X is a divalent $C_1$-$C_6$ alkyl, $C_2$-$C_6$ alkenyl or $C_2$-$C_6$ alkynyl group and R is aryl or heteroaryl.

Preferred substituents include halogen, for example chlorine, fluorine and bromine, —SH, hydroxy, $C_1$-$C_6$ alkyl, for example t-butyl, methyl, —$CF_3$, —$CCl_3$, —$CH_2$OH, —$CH_2NMe_2$, —$CH_2NH_2$ and —($CH_{23}$OMe, aryl, heteroaryl, 3- to 6-membered heterocyclyl, $C_3$-$C_6$ carbocyclyl, nitro, cyano, $C_1$-$C_6$ alkoxy, $C_2$-$C_6$ alkenyloxy, $C_1$-$C_6$ alkylthio, $C_2$-$C_6$ alkenylthio, —OR, —SR, —COR', —$CO_2$R", —CONR'''R"" and —NR'''R"" wherein R is aryl or —($C_1$-$C_6$ alkyl)-aryl, R' is selected from R or $C_1$-$C_6$ alkyl, R" is selected from R' and hydrogen and R''' and R"" are the same or different and are selected from R', hydrogen and hydroxy, and —S—($C_1$-$C_6$ alkyl)-CO—R, wherein R is aryl or $C_1$-$C_6$ alkyl.

More preferred substituents include halogen, for example fluorine, chlorine and bromine, —SH, hydroxy, $C_1$-$C_6$ alkyl, for example, methyl, ethyl, propyl, n-butyl, t-butyl, —$CF_3$, —$CCl_3$, —$CH_2$OH, —$CH_2NMe_2$, —$CH_2NH_2$ and —($CH_2$)$_3$OMe, aryl, for example phenyl, $C_3$-$C_6$ carbocyclyl, for example cyclohexane, $C_1$-$C_6$ alkoxy, $C_2$-$C_6$ alkenyloxy, $C_1$-$C_6$ alkylthio, for example methylthio and ethylthio, $C_2$-$C_6$ alkenylthio, for example ethenylthio and propenylthio, —$CO_2$H, —$CO_2C_1$-$C_6$ alkyl), for example —$CO_2$Me and —$CO_2$Et, —CONH-aryl, for example —CONH-phenyl, —CONH—OH, —CONH—($C_1$-$C_6$ alkyl), for example —CONH($CH_2$)$_2NMe_2$, —CON(OH)($C_1$-$C_6$ alkyl)-aryl, for example —CON(OH)—$CH_2$-phenyl, NR'R" wherein R' and R" are the same or different and are hydrogen or $C_1$-$C_6$ alkyl, for example $NH_2$, $NMe_2$ and NHEt, —S—($C_1$-$C_6$ alkyl)-aryl for example —S—$CH_2$-phenyl, and —S—($C_1$-$C_6$ alkyl)-CO—R wherein R is aryl, for example phenyl, or $C_1$-$C_6$ alkyl, for example ethyl or t-butyl.

When a said aryl, heteroaryl, $C_3$-$C_6$ carbocyclic or 3- to 6-membered heterocyclic group is substituted by a substituent which includes an aryl, heteroaryl, carbocyclic or heterocyclic moiety, the aryl, heteroaryl, carbocyclic or heterocyclic moiety in the substituent is typically unsubstituted or substituted by one or more further substituent selected from halogen, hydroxy, $C_1$-$C_6$ alkyl, for example $C_1$-$C_6$ haloalkyl, $C_1$-$C_6$ alkoxy, for example $C_1$-$C_6$ haloalkoxy and —NR'R" wherein R' and R" are the same or different and represent hydrogen or $C_1$-$C_6$ alkyl. Typically, these further substituents are themselves unsubstituted.

As used herein, a said alkoxy group is typically a said alkyl group attached to an oxygen atom. A preferred alkoxy group is a haloalkoxy group. A said alkenyloxy group is typically a said alkenyl group attached to an oxygen atom. A said alkynyloxy group is typically a said alkynyl group attached to an oxygen atom. A said alkylthio group is typically a said alkyl group attached to a thio group. A said alkenylthio group is typically a said alkenyl group attached to a thio group. A said alkynylthio group is typically a said alkynyl group attached to a thio group.

A haloalkyl or haloalkoxy group is typically a said alkyl or alkoxy group substituted by one or more said halogen atoms. Typically it is substituted by 1, 2 or 3 said halogen atoms. Preferred haloalkyl and haloalkoxy groups include perhaloalkyl and perhaloalkoxy groups such as —$CX_3$ and —$OCX_3$ wherein X is a said halogen atom. Particularly preferred haloalkyl groups are $CF_3$ and $CCl_3$. Particularly preferred haloalkoxy groups are —$OCF_3$ and —$OCCl_3$.

Preferably $R_1$ is $C_1$-$C_6$ alkyl, aryl or —($C_1$-$C_6$ alkyl)-aryl. More preferably, $R_1$ is $C_1$-$C_6$ alkyl, phenyl or benzyl. Most preferably, $R_1$ is benzyl. Typically, the group $R_1$ is unsubstituted or is substituted by one or more, for example 1, 2 or 3, selected from halogen, hydroxyl, $C_1$-$C_6$ alkyl, $C_1$-$C_6$ alkoxy and —NR'R" wherein R' and R" are the same or different and are selected from hydrogen and $C_1$-$C_6$ alkyl.

$R_1$ is preferably aryl, heteroaryl, 3- to 6-membered heterocyclyl, $C_3$-$C_6$ carbocyclyl, $C_1$-$C_6$ alkyl, $C_2$-$C_6$ alkenyl, —CONR'R" or —$CO_2$R' wherein each R' and R" are the same or different and are selected from hydrogen, $C_1$-$C_6$ alkyl, aryl and heteroaryl.

More preferably, $R_2$ is aryl, for example phenyl, heteroaryl, for example thienyl, furanyl and oxadiazolyl, 3- to 6-membered heterocyclyl, $C_1$-$C_6$ alkyl, for example, methyl, n-butyl, t-butyl and —$(CH_2)_4$NHEt, or —CONR'R" wherein R' and R" are the same or different and are selected from hydrogen, $C_1$-$C_6$ alkyl, aryl and heteroaryl, for example —CONH$(CH_2)_2$NMe$_2$, —CO—NH-phenyl and —CONH—X wherein X is isoxazolyl or pyridyl. Typically, these more preferred $R_2$ substituents are selected from aryl, for example phenyl, heteroaryl, for example furanyl and oxadiazolyl, 3- to 6-membered heterocyclyl, $C_1$-$C_6$ alkyl, for example, methyl, n-butyl, t-butyl and —$(CH_2)_4$NHEt, or —CONR'R" wherein R' and R" are the same or different and are selected from hydrogen, $C_1$-$C_6$ alkyl and aryl, for example —CONH$(CH_2)_2$NMe$_2$ and —CO—NH-phenyl.

Typically, when $R_2$ is a heteroaryl group, it is an oxadiazolyl group. Typically, when $R_2$ is an alkyl group, it is not substituted by a methylamino or dimethylamino group. More typically, when $R_2$ is an alkyl group it is not substituted by a group of formula —NR'R" wherein R' and R" are the same or different and each represent hydrogen or $C_1$-$C_6$ alkyl.

When $R_3$ and $R_4$ do not, together with the carbon atoms to which they are attached, form a phenyl group, $R_3$ is preferably hydrogen. $R_4$ is preferably $C_1$-$C_6$ alkyl, aryl, heteroaryl, —CONR'—NR"COR, —CONR'—NR"CS—R, —$CO_2$R', —CONR'R", —CONR'—NR"CO—NR'"R"" or —CONR'—NR"CS—NR'"R"" wherein each R is the same or different and is selected from $C_1$-$C_6$ alkyl, aryl, —($C_1$-$C_6$ alkyl)-aryl and heteroaryl, and each R', R", R'" and R"" is the same or different and is selected from hydrogen, $C_1$-$C_6$ alkyl, aryl, $C_1$-$C_6$ alkyl)-aryl and heteroaryl. Typically, these preferred $R_4$ substituents are selected from $C_1$-$C_6$ alkyl, aryl, heteroaryl, —CONR'—NR"COR, —CONR'—NR"CS—R, $CO_2$R', —CONR'R", —CONR'—NR"CO—NR'"R"" or —CONR'—NR"CS—NR'"R"" wherein each R is the same or different and is selected from $C_1$-$C_6$ alkyl and aryl and each R', R", R'" and R"" is the same or different and is selected from hydrogen, $C_1$-$C_6$ alkyl and aryl.

More preferably, $R_4$ is $C_1$-$C_6$ alkyl, for example methyl, heteroaryl, for example triazolyl, —CONR'—NR"COR, —CONR'R", —CONR'NR"CO—NR'"R"" or —CONR'—NR"CS—NR'"R"" wherein R is $C_1$-$C_6$ alkyl or aryl and each R', R", R'" and R"" is the same or different and is selected from hydrogen, $C_1$-$C_6$ alkyl aryl, —($C_1$-$C_6$ alkyl)-aryl and heteroaryl. Typically, the —CONR'—NR"COR moiety is —CONH—NHCO-phenyl or —CONH—NHCO-tBu. Typically, the —CONR'R" moiety is —CO—NH—Z wherein Z is H, phenyl, benzyl, -ethyl-phenyl, pyridyl, thiazolyl or oxadiazolyl. More typically, the moiety —CONR'R" is —CONH-phenyl or —CONH$_2$. Typically, the —CONR'—NR"CONR'"R"" moiety is CONH—NHCO—NH-phenyl. Typically, the —CONR'—NR"CS—NR'"R"" moiety is —CONH—NHCS—NHMe.

Typically, when $R_4$ is an alkyl group, it is not substituted by a methylamino or dimethylamino group. More typically, when $R_4$ is an alkyl group, it is not substituted by a group of formula —NR'R" wherein R' and R" are the same or different and each represent hydrogen or $C_1$-$C_6$ alkyl.

Preferred compounds of the invention are compounds of formula (I), as defined above, and pharmaceutically acceptable salts thereof, wherein:

$R_1$ is $C_1$-$C_6$ alkyl, aryl or $C_1$-$C_6$ alkyl)-aryl;

$R_2$ is aryl, heteroaryl, 3- to 6- membered heterocyclyl, $C_3$-$C_6$ carbocyclyl, $C_1$-$C_6$ alkyl, $C_2$-$C_6$ alkenyl, —CONR'R" or —$CO_2$R' wherein each R' and R" are the same or different and are selected from hydrogen, $C_1$-$C_6$ alkyl, aryl and heteroaryl; and either $R_3$ and $R_4$, together with the carbon atoms to which they are attached, form a phenyl group or $R_3$ is hydrogen and $R_4$ is $C_1$-$C_6$ alkyl, aryl, heteroaryl, —CONR'—NR"COR, —CONR'—NR"CS—R, —$CO_2$R', —CONR'R", —CONR'—NR"CO—NR'"R"" or —CONR'—NR"CS—NR'"R"" wherein each R is the same or different and is selected from $C_1$-$C_6$ alkyl, aryl, —($C_1$-$C_6$ alkyl)-aryl and heteroaryl and each R', R", R'" and R"" is the same or different and is selected from hydrogen, $C_1$-$C_6$ alkyl, aryl, —($C_1$-$C_6$ alkyl)-aryl and heteroaryl.

Further preferred compounds of the invention are compounds of formula (1), as defined above, and pharmaceutically acceptable salts thereof, wherein:

$R_1$ is $C_1$-$C_6$ alkyl, phenyl or benzyl;

$R_2$ is aryl for example phenyl, heteroaryl, for example thienyl, furanyl and oxadiazolyl, 3- to 6-membered heterocyclyl, $C_1$-$C_6$ alkyl, for example, methyl, n-butyl, t-butyl and —$(CH_2)_4$NHEt, or —CONR'R" wherein R' and R" are the same or different and are selected from hydrogen, $C_1$-$C_6$ alkyl, aryl and heteroaryl, for example —CONH$(CH_2)_2$NMe$_2$, —CO—NH-phenyl and —CONH—X wherein X is isoxazolyl or pyridyl; and either $R_3$ and $R_4$, together with the carbon atoms to which they are attached, form a phenyl group, or $R_3$ is hydrogen and $R_4$ is $C_1$-$C_6$ alkyl, for example methyl, heteroaryl, for example triazolyl, —CONR'—N"COR, —CONR'R", —CONR'NR"CO—NR'"R"" or —CONR'—NR"CS—NR'"R"" wherein R is $C_1$-$C_6$ alkyl or aryl and each R', R", R'" and R"" is the same or different and is selected from hydrogen, $C_1$-$C_6$ alkyl, aryl, —($C_1$-$C_6$ alkyl)-aryl and heteroaryl.

In a further preferred embodiment of the invention, $R_3$ and $R_4$, together with the carbon atoms to which they are attached, form a phenyl group. This phenyl group may be unsubstituted or substituted at any position. Typically, it is unsubstituted or carries 1, 2 or 3 substituents. Suitable substituents include those mentioned above as appropriate substituents for an aryl group. Preferred substituents include $C_1$-$C_6$ alkyl, for example methyl, ethyl —$CF_3$ and —$CCl_3$, halogen, for example chlorine, hydroxy, $C_1$-$C_6$ alkoxy, for example methoxy and ethoxy, and —NR'R" wherein R' and R" are the same or different and are selected from hydrogen and $C_1$-$C_6$ alkyl. Thus, preferred indazole compounds of the invention have the formula (Ia) as set out below.

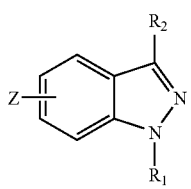

(Ia)

wherein $R_1$ and $R_2$ are as defined above and Z denotes one or more, preferably one or two, selected from hydrogen, $C_1$-$C_6$ alkyl, for example methyl, ethyl, —$CF_3$ and —$CCl_3$, halogen, for example chlorine, hydroxy, $C_1$-$C_6$ alkoxy, for example methoxy or ethoxy, and —NR'R" wherein R' and R" are the same or different and are selected from hydrogen and $C_1$-$C_6$ alkyl.

In a further preferred embodiment of the invention, $R_4$ is a thiosubstituted triazole group. Such compounds have the formula (Ib) and, together with their pharmaceutically acceptable salts, constitute preferred compounds of the invention

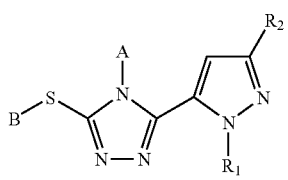

(Ib)

wherein:

$R_1$ and $R_2$ are as defined above;

A is hydrogen, $C_1$-$C_6$ alkyl, $C_2$-$C_6$ alkenyl, aryl, heteroaryl, 3- to 6-membered heterocyclyl or $C_3$-$C_6$ carbocyclyl; and B is hydrogen, $C_1$-$C_6$ alkyl, $C_2$-$C_6$ alkenyl, $C_2$-$C_6$ alkynyl, aryl, heteroaryl, —XY wherein X is a divalent $C_1$-$C_6$ alkyl, $C_2$-$C_6$ alkenyl or $C_2$-$C_6$ alkynyl group and Y is an aryl or heteroaryl group, or —X'—COR or —X'—$CO_2$R wherein X' is a divalent $C_1$-$C_6$ alkyl, $C_2$-$C_6$ alkenyl or $C_2$-$C_6$ alkynyl group and R is $C_1$-$C_6$ alkyl, aryl or heteroaryl.

Typically, in the formula (Ib), A is aryl for example phenyl, $C_3$-$C_6$ carbocyclyl for example cyclohexyl, or $C_1$-$C_6$ akyl, for example methyl. Typically, B is hydrogen, $C_1$-$C_6$ alkyl, for example methyl and ethyl, $C_2$-$C_6$ alkenyl $C_2$-$C_6$ alkynyl for example propynyl, aryl, for example phenyl, —($C_1$-$C_6$ akyl)-aryl, for example benzyl, —($C_1$-$C_6$ alkyl)$CO_2$R or —($C_1$-$C_6$ alkyl)-COR wherein R is $C_1$-$C_6$ alkyl, for example ethyl and t-butyl, or aryl, for example phenyl.

Preferred compounds of formula (Ib) are compounds in which:

$R_1$ is $C_1$-$C_6$ alkyl or $C_1$-$C_6$ alkyl)-aryl, for example benzyl;

$R_2$ is hydrogen or $C_1$-$C_6$ alkyl;

A is aryl, for example phenyl, $C_3$-$C_6$ carbocyclyl, for example cyclohexyl, or $C_1$-$C_6$ alkyl, for example methyl; and B is hydrogen, $C_1$-$C_6$ alkyl, for example methyl and ethyl, $C_2$-$C_6$ alkenyl, $C_2$-$C_6$ alkynyl, for example propynyl, aryl, for example phenyl, —($C_1$-$C_6$ alkyl)-aryl, for example benzyl, —($C_1$-$C_6$ alkyl)-$CO_2$R or —($C_1$-$C_6$ akyl)-COR wherein R is $C_1$-$C_6$ alkyl for example ethyl and t-butyl, or aryl, for example phenyl;

and pharmaceutically acceptable salts thereof.

In a further preferred embodiment of the invention, $R_2$ is a carboxyamide group. Such compounds have the formula (Ic) and, together with their pharmaceutically acceptable salts, constitute preferred compounds of the invention.

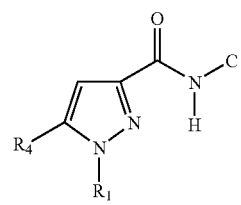

(Ic)

wherein:

$R_1$ and $R_4$ are as defined above; and

C is aryl, heteroaryl, 3- to 6-membered heterocyclyl or $C_3$-$C_6$ carbocyclyl.

Preferably, C in the formula (Ic) is an aryl or heteroaryl group optionally substituted with 1 or 2 of the substituents mentioned above as suitable for an aryl or heteroaryl group.

Preferred compounds of formula (Ic) are compounds in which $R_1$ is aryl, for example phenyl, —($C_1$-$C_6$-alkyl)-aryl, for example benzyl, or $C_1$-$C_6$ alkyl;

$R_4$ is aryl, for example phenyl, or $C_1$-$C_6$ alkyl; and

C is aryl or heteroaryl and pharmaceutically acceptable salts thereof.

In a further preferred embodiment of the invention, $R_4$ is a carboxyamide group. Such compounds have the formula (Id) and, together with their pharmaceutically acceptable salts, constitute preferred compounds of the invention

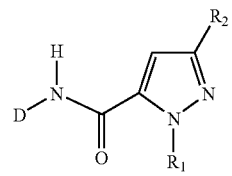

(Id)

wherein:

$R_1$ and $R_2$ are as defined above; and

D is aryl, heteroaryl, 3- to 6-membered heterocyclyl, $C_3$-$C_6$ carbocyclyl, —XY wherein X is a divalent $C_1$-$C_6$ alkyl, $C_2$-$C_6$ alkenyl or $C_1$-$C_6$ alkynyl group and Y is aryl, heteroaryl, 3- to 6-membered heterocyclyl or $C_3$-$C_6$ carbocyclyl, or —NR"CO—N'''R'''' wherein R" and R''' are the same or different and are hydrogen or C$_1$-C$_6$ alkyl and R"" is hydrogen, C$_1$-C$_6$ alkyl or aryl, for example phenyl.

Preferably, D in the formula (Id) is an aryl, heteroaryl or —(C$_1$-C$_6$ alkyl)-aryl group optionally substituted by 1 or 2 of the substituents mentioned above as suitable for an aryl or heteroaryl group, or is —NH—CO—NH-aryl, for example —NH—CO—NH-(3-chlorophenyl).

Preferred compounds of formula (Id) are compounds in which
- R$_1$ is C$_1$-C$_6$ alkyl, aryl, for example phenyl, or —(C$_1$-C$_6$ alkyl)-aryl, for example benzyl;
- R$_2$ is C$_1$-C$_6$ alkyl, aryl, for example phenyl, or heteroaryl, for example thienyl; and
- D is aryl, for example phenyl, heteroaryl, for example pyridyl, thiazolyl and oxadiazolyl or —(C$_1$-C$_6$ alkyl)-aryl, for example benzyl and -ethyl-phenyl and pharmaceutically acceptable salts thereof.

For the avoidance of doubt any of the moieties present in the substituents of the preferred compounds of formulae (Ia), (Ib), (Ic) and (Id) may be unsubstituted or substituted by one or more of the substituents discussed above as suitable for the moiety in question.

Typically, in the compounds of the invention, when R$_1$ is benzyl and R$_3$ and R$_4$, together with the carbon atoms to which they are attached, form a phenyl group, R$_2$ is not furanyl or phenyl. More typically, R$_2$ is not furanyl, phenyl, pyrrolyl, or thienyl. In other words, the compounds of the invention are typically not 1-benzyl-3-(furanyl, phenyl, pyrrolyl or thienyl)-indazoles. Preferably, the compounds of the invention which are indazoles do not carry an aryl or heteroaryl group at the 3-position. In other words, the compounds of the invention are preferably not 1-benzyl-3-aryl-indazoles or 1-benzyl-3-heteroaryl-indazoles.

The present invention includes pharmaceutically acceptable salts of the compounds of the invention. Suitable salts include salts with pharmaceutically acceptable acids, both inorganic acids such as hydrochloric, sulphuric, phosphoric, diphosphoric, hydrobromic or nitric acid and organic acids such as citric, fumaric, maleic, malic, ascorbic, succininc, tartaric, benzoic, acetic, methanesulphoric, ethanesulphonic, benzenesulphonic or p-toluenesulphonic acid. Salts may also be formed with pharmaceutically acceptable bases such as alkali metal (eg sodium or potassium) and alkali earth metal (eg calcium or magnesium) hydroxides and organic bases such as alkyl amines, aralkyl amines or heterocyclic amines.

Particularly preferred compounds of the invention are:
1-Benzyl-3-(5-hydroxymethyl-2-furyl)-1H-indazole
1-Benzyl-3-(5-methoxycarbonyl-2-furyl)-1H-indazole
1-Benzyl-3-[3-aminomethyl-1,2,4oxadiazol-5-yl]indazole
1-Benzyl-3-(5-hydroxylaminocarbonyl-2-furyl)-1H indazole
1-Benzyl-3-[3-(N,N-dimethylaminomethyl)-1,2,4-oxadiazol-5-yl]indazole
2-Benzyl-5-tert-butyl-2H-pyrazole-3-carboxylic acid N'-(3-chlorophenylcarbamoyl) hydrazide
2-{5-[5-tert-Butyl-2-(4-fluoro-benzyl)-2H-pyrazol-3-yl]-4methyl-4H-[1,2,4]triazol-3-ylsulfanyl}-1-(4-chloro-phenyl)-ethanone
3-Benzylsulfanyl-5-[5-tert-butyl-2-(4-fluoro-benzyl)-2H-pyrazol-3-yl]4-methyl-4H-[1,2,4]triazole
2-Benzyl-5-tert-butyl-2H-pyrazole-3-carboxylic acid (4-chloro-phenyl)-amide
[N-Ethyl-(4-aminobutyl)]-1-benzylindazole
1-Benzyl-3-[N-2-N,N-dimethylaminoethyl)carboxamido]indazole
5-(1-Benzyl-1H-indazol-3-yl)-furan-2-carboxylic acid benzyl-hydroxy-amide
5-(1-Benzyl-1H-indazol-3-yl)-furan-2-carboxylic acid N-benzylhydroxyl amine ester
2-Benzyl-5-tert-butyl-2H-pyrazole-3-carboxylic acid (4-chloro-phenyl)-amide
2-Benzyl-5-tert-butyl-2H-pyrazole-3-carboxylic acid (2-chloro-phenyl)amide
2-Benzyl-5-tert-butyl-2H-pyrazole-3-carboxylic acid p-tolylamide
2-Benzyl-5-tert-butyl-2H-pyrazole-3-carboxylic acid (4-bromo-3-chloro-phenyl)-amide
2-Benzyl-5-tert-butyl-2H-pyrazole-3-carboxylic acid N'-[1-(4chloro-phenyl)-methanoyl]-hydrazide
2-Benzyl-5-tert-butyl-2H-pyrazole-3-carboxylic acid N'-(phenylcarbamoyl)hydrazide
2-Benzyl-5-tert-butyl-2H-pyrazole-3-carboxylic acid N'-(3-chlorobenzoyl)hydrazide
2-Benzyl-5-tert-butyl-2H-pyrazole-3-carboxylic acid amide
1-tert-Butyl-5-methyl-1H-pyrazole-3-carboxylic acid (4chloro-phenyl)-amide
1-tert-Butyl-5-methyl-1H-pyrazole-3-carboxylic acid (4-tert-butyl-phenyl)-amide
5-tert-Butyl-2-methyl-2H-pyrazole-3-carboxylic acid phenylamide
5-tert-Butyl-2-methyl-2H-pyrazole-3-carboxylic acid (4chloro-phenyl)-amide
5-tert-Butyl-2-methyl-2H-pyrazole-3-carboxylic acid (4tert-butyl-phenyl)-amide
5-Methyl-2-(4-methyl-benzyl)-2H-pyrazole-3-carboxylic acid (4-chloro-phenyl)-amide
5-Methyl-2-(methyl-benzyl)-2H-pyrazole-3-carboxylic acid (2-chloro-phenyl)-amide
5-Methyl-2-(4-methyl-benzyl)-2H-pyrazole-3-carboxylic acid (3-trifluoromethyl-phenyl)-amide
5-Methyl-2-(4-methyl-benzyl)-2H-pyrazole-3-carboxylic acid p-tolylamide
5-Methyl-2-(3-trifluoromethyl-benzyl)-2H-pyrazole-3-carboxylic acid (2,4-dichloro-phenyl)-amide
5-Methyl-2-(3-trifluoromethyl-benzyl)-2H-pyrazole-3-carboxylic acid (4-cyclohexyl-phenyl)-amide
5-Methyl-1-(4-methyl-benzyl)-1H-pyrazole-3-carboxylic acid (4-bromo-phenyl)-amide
5-Methyl-1-(4-methyl-benzyl)-1H-pyrazole-3-carboxylic acid phenylamide
1-(2,6-Dichlorobenzyl)-5-methyl-1H-pyrazole-3-carboxylic acid (3-methyl-phenyl)-amide
1-(2,6-Dichloro-benzyl)-5-methyl-1H-pyrazole-3-carboxylic acid (4-tert-butyl-phenyl)-amide
2-[5-(2-Ethyl-5-methyl-2H-pyrazol-3-yl)-4-phenyl4H-[1,2,4]triazol-3-ylsulfanyl]-1-phenyl-ethanone
2-[4-(4Chloro-phenyl)-5-(2-ethyl-5-methyl-2H-pyrazol-3-yl)-4H-[1,2,4]triazol-3-ylsulfanyl]-1-phenyl-ethanone
2-[5-(2-Ethyl-5-methyl-2H-pyrazol-3-yl)-4-(3-methoxypropyl)-4H-[1,2,4]triazol-3-ylsulfanyl]-1-phenyl-ethanone
2-[5-(2-Ethyl-5-methyl-2H-pyrazol-3-yl)-4-(3-trifluoromethyl-phenyl)-4H-[1,2,4]triazol-3-ylsulfanyl]-1-phenyl-ethanone
5-[5-tert-Butyl-2-(4fluorobenzyl)-2H-pyrazol-3-yl]-4-methyl-4H-[1,2,4]triazole-3-thiol 3-[5-tert-Butyl-2-(4-fluorobenzyl)-2H-pyrazol-3-yl]-4methyl-5-methylsulfanyl-4H-[1,2,4]triazole
3-Allylsulfanyl-5-[5-tert-butyl-2-(4-fluoro-benzyl)-2H-pyrazol-3-yl]-4-methyl-4H-[1,2,4]triazole
3-Benzylsulfanyl-5-[5-tert-butyl-2-(4-fluoro-benzyl)-2H-pyrazol-3-yl]-4-methyl-4H-[1,2,4]triazole
2-{5-[5-tert-Butyl-2-(4-fluoro-benzyl)-2H-pyrazol-3-yl]-4-methyl-4H-[1,2,4]triazol-3-ylsulfanyl}-1-phenyl-ethanone
2-{5-[5-tert-Butyl-2-(4-fluoro-benzyl)-2H-pyrazol-3-yl]-4methyl-4H-[1,2,4]triazol-3-ylsulfanyl}-1-(4-chloro-phenyl)ethanone
{5-[5-tert-Butyl-2-(4-fluoro-benzyl)-2H-pyrazol-3-yl]-4-methyl-4H-[1,2,4] triazol-3-ylsulfnyl}-acetic acid ethyl ester
1-{5-[5-tert-Butyl-2-(4-fluoro-benzyl)-2H-pyrazol-3-yl]-4-methyl-4H-[1,2,4] triazol-3-ylsulfanyl}-3,3-dimethyl-butan-2-one
2-Ethyl-5-methyl-2H-pyrazole-3-carboxylic acid N'-[1-(3-chloro-phenyl)-methanoyl]-hydrazide
Benzoic acid N'-[1-(2-benzyl-5-tert-butyl-2H-pyrazol-3-yl)-methanoyl]-hydrazide
2-Benzyl-5-tert-butyl-2H-pyrazole-3-carboxylic acid N'-[1-(4-trifluoromethyl-phenyl)-methanoyl]-hydrazide
2-Benzyl-5-tert-butyl-2H-pyrazole-3-carboxylic acid N'-(2,2-dimethyl-propanoyl)-hydrazide
2-Benzyl-5-tert-butyl-2H-pyrazole-3-carboxylic acid N'-(2,6-dimethylphenylcarbamoyl)hydrazide
2-Benzyl-5-tert-butyl-2H-pyrazole-3-carboxylic acid N'-(3-trifluoromethylphenylcarbamoyl)hydrazide
2-Benzyl-5-tert-butyl-2H-pyrazole-3-carboxylic acid N'-(methylthiocarbamoyl)hydrazide
3-(Benzylthio)-5-(1-ethyl-3-methyl-1H-pyrazol-5-yl)-4-phenyl-4H-1,2,4-triazolehemihydrate
5-[3-(tert-Butyl)-1-(3-methylbenzyl)pyrazol-5-yl]-4-cyclohexyl-1,2,4-triazole-3-thiol
5-[3-tert-Butyl-1-(2,4-dichlorobenzyl)pyrazol-5-yl]-4-methyltriazole-3-thiol
Ethyl 2-([5-[3-(tert-butyl)-1-(3-methylbenzyl)-1H-pyrazol-5-yl]-4-cyclohexyl-4H-1,2,4-triazol-3-yl]thio)acetate
3-[3-tert-Butyl)-1-(2,4-dichlorobenzyl)-1H-pyrazol-5-yl]-4-phenyl-5-(prop-2-ynylthio)-4H-1,2,4-triazole
2-Benzyl-5-tert-butyl-2H-pyrazole-3-carboxylic acid phenylamide
2-Benzyl-5-tert-butyl-2H-pyrazole-3-carboxylic acid benzylamide
1-(4-Chloro-phenyl)-5-phenyl-1H-pyrazole-3-carboxylic acid phenylamide
5-tert-Butyl-2-(2,4-dichloro-benzyl)-2H-pyrazole-3-carboxylic acid (4-methoxy-phenyl)-amide
2-Ethyl-5-thiophen-2-yl-2H-pyrazole-3-carboxylic acid (4-chloro-phenyl)-amide
(S)-5-tert-Butyl-2-(2,4-dichloro-benzyl)-2H-pyrazole-3-carboxylic acid (4-chloro-phenyl)-amide
5-tert-Butyl-2-(2,4-dichloro-benzyl)-2H-pyrazole-3-carboxylic acid phenethyl-amide
(S)-2-Ethyl-5-thiophen-2-yl-2H-pyrazole-3-carboxylic acid phenethyl-amide
5-tert-Butyl-2-(2,4-dichloro-benzyl)-2H-pyrazole-3-carboxylic acid phenylamide
5-tert-Butyl-2-(2,4-dichloro-benzyl)-2H-pyrazole-3-carboxylic acid benzylamide
1-(4-Chloro-phenyl)-5-phenyl-1H-pyrazole-3-carboxylic acid (4-dimethylamino-phenyl)-amide
1-(4-Chloro-phenyl)-5-phenyl-1H-pyrazole-3-carboxylic acid (4-tert-butyl-phenyl)-amide
2-tert-Butyl-5-methyl-2H-pyrazole-3-carboxylic acid (4-tert-butyl-phenyl)-amide
2-tert-Butyl-5-methyl-2H-pyrazole-3-carboxylic acid (3,4-dichloro-phenyl)-amide
5-tert-Butyl-2-methyl-2H-pyrazole-3-carboxylic acid (3,4-dichloro-phenyl)-amide
2-Benzyl-5-tert-butyl-2H-pyrazole-3-carboxylic acid (3,4-dichloro-phenyl)-amide
2-Benzyl-5-tert-butyl-2H-pyrazole-3-carboxylic acid (4-tert-butyl-phenyl)-amide
5-tert-Butyl-2-methyl-2H-pyrazole-3-carboxylic acid (4-tert-butyl-phenyl)-amide
2-Benzyl-5-tert-butyl-2H-pyrazole-3-carboxylic acid (4-dimethylamino-phenyl)-amide
2-Benzyl-5-tert-butyl-2H-pyrazole-3-carboxylic acid (3-oxazol-5-yl-phenyl)-amide
5-tert-Butyl-2-methyl-2H-pyrazole-3-carboxylic acid (3-oxazol-5-yl-phenyl)-amide
1-(4-Chloro-phenyl)-5-phenyl-1H-pyrazole-3-carboxylic acid (5-tert-butyl-isoxazol-3-yl)-amide
2-tert-Butyl-5-methyl-2H-pyrazole-3-carboxylic acid (4-phenylcarbamoyl-phenyl)-amide
2-Benzyl-5-tert-butyl-2H-pyrazole-3-carboxylic acid (3-phenylcarbamoyl-phenyl)-amide
5-tert-Butyl-2-methyl-2H-pyrazole-3-carboxylic acid (3-phenylcarbamoyl-phenyl)-amide
2-Benzyl-5-tert-butyl-2H-pyrazole-3-carboxylic acid (6-chloro-pyridin-3-yl)-amide
1-tert-Butyl-5-methyl-1H-pyrazole-3-carboxylic acid (6-chloro-pyridin-3-yl)-amide
1-tert-Butyl-5-methyl-1H-pyrazole-3-carboxylic acid (4-acetylamino-phenyl)-amide
1-tert-Butyl-5-methyl-1H-pyrazole-3-carboxylic acid (3-benzyloxy-pyridin-2-yl)-amide
5-Methyl-1-(4-methyl-benzyl)-1H-pyrazole-3-carboxylic acid (4-acetylamino-phenyl)amide
5-tert-Butyl-2-(2,4-dichloro-benzyl)-2H-pyrazole-3-carboxylic acid (4-acetylamino-phenyl)-amide
2-Ethyl-5-thiophen-2-yl-2H-pyrazole-3-carboxylic acid (4-acetylamino-phenyl)amide
5-tert-Butyl-2-(2,4-dichloro-benzyl)-2H-pyrazole-3-carboxylic acid (4-(pyridin-3-yl) thiazol-2-yl)-amide
2-Ethyl-5-thiophen-2-yl-2H-pyrazole-3-carboxylic acid (4-pyridin-3-yl) thiazol-2-yl)-amide
2-Benzyl-5-tert-butyl-2H-pyrazole-3-carboxylic acid (4-acetylaminophenyl)-amide
5-tert-Butyl-2-methyl-2H-pyrazole-3-carboxylic acid (4(pyridin-3-yl) thiazol-2-yl)amide
5-tert-Butyl-2-methyl-2H-pyrazole-3-carboxylic acid [3-(4-methoxy-benzyl)-[1,2,4]oxadiazol-5-yl]-amide and pharmaceutically acceptable salts thereof.

The compounds of formula (I) in which $R_4$ is $C_1$-$C_6$ alkyl, $C_2$-$C_6$ alkenyl, $C_2$-$C_6$ alkynyl, aryl, heteroaryl or 3- to 6-membered heterocyclyl may be prepared by the process shown in Scheme I below. These reactions are described in Grandberg I, et al. Zhur. Obshchei Khim. 30, 2920-5 (1960) (CA61, 16517f) and Teremt'ev, I, Ibid 30, 2925-31 (CA61, 16518c).

Scheme 1

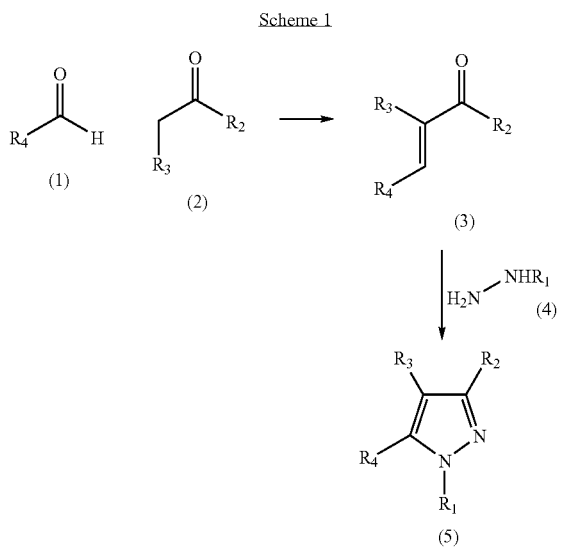

In Scheme 1, an aldehyde of formula (1), wherein $R_4$ is $C_1$-$C_6$ alkyl $C_2$-$C_6$ alkenyl, $C_2$-$C_6$ alkynyl, aryl, heteroaryl or 3- to 6-membered heterocyclyl, can be reacted with a ketone of formula (2), in which $R_2$ and $R_3$ are as defined in the formula (I). This condensation is typically conducted in the presence of a base. Suitable bases include sodium hydride, potassium tert butoxide, sodium ethoxide and lithium diisopropylamide. A preferred base is sodium methoxide. The reaction typically takes place at from 0 to 5° C. A compound of formula (3) is thereby prepared.

The compound of formula (3) can be reacted with a hydrazine of formula (4), wherein $R_1$ is as defined in the formula (I), to give a pyrazole of formula (5). This reaction may be carried out in a solvent such as methanol at reflux for from 1 to 4 hours.

The compounds of the formulae (1), (2) and (4) are known compounds or may be prepared by analogy with known methods.

Compounds in which $R_4$ is hydrogen can be prepared by analogy with known methods for preparing pyrazoles. For example, a compound of formula (6).

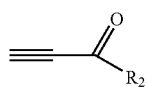
(6)

wherein $R_2$ is as defined above, can be reacted with hydrazine to give a compound of formula (I) in which $R_1$, $R_3$ and $R_4$ are hydrogen. Alternatively, a compound of formula (6a)

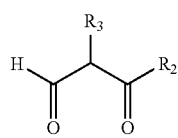
(6a)

wherein $R_2$ and $R_3$ are as defined in the formula (I), can be reacted with hydrazine to give a compound of formula (I) in which $R_1$ and $R_4$ are hydrogen.

Compounds of formula (I) in which $R_1$ is hydrogen can be converted to corresponding compounds of formula (I) in which $R_1$ is $C_1$-$C_6$ alkyl or —($C_1$-$C_6$ alkyl)-aryl by alkylation with a compound of formula $R_1$-L in which $R_1$ is $C_1$-$C_6$ alkyl or —($C_1$-$C_6$ alkyl)-aryl and L is a leaving group such as bromine. Typically, the reaction takes place in the presence of a base such as sodium hydride.

Compounds of formula (I) in which $R_1$ is hydrogen can be converted to corresponding compounds of formula (I) in which $R_1$ is aryl by boronic acid coupling, i.e. by reaction with Ar—B(OH)$_2$ in the presence of copper acetate. The reaction can be conducted under standard conditions known to those of skill in the art.

The compounds of formula (I) in which $R_4$ is —CONR'—NR"COR, —CONR'—NR"CS—R, —$CO_2$R', —CONR'—NR"—$CO_2$R', —CONR'—NR"—CS—OR', —CONR'R", —CONR'—NR"CO—NR'''R'''' and —CONR'—NR"CS—NR'''R'''', wherein R, R', R", R''' and R'''' are as defined above, can be prepared by preparing a compound of formula (5) in which $R_4$ is 2-furyl according to Scheme 1 above, and oxidising the thus obtained compound of formula (5) to give a compound of formula (I) in which $R_4$ is —$CO_2$H. This oxidation can be effected using a strong oxidising agent such as potassium permanganate. For example, the 2-furyl compounds can be stirred with $KMnO_4$ in acetone/benzene at from 18 to 20° C. for from 1 to 4 hours, then stirred at room temperature for from 1 to 3 days, to give the corresponding carboxylic acids.

The thus obtained carboxylic acids can be esterified with alcohols of formula HOR, wherein R is as defined above, by known methods, or may be condensed with compounds of formulae HNR'R", HR'—NR"COR, HNR'—NR"CS—R, HNR'—NR"—$CO_2$R', HNR'—NR"CO—NR'''R'''', HNR'—NR"—CS—OR' or HNR'—N"—CS—NR'''R'''', wherein R, R', R", R''' and R'''' are as defined above, to give compounds of formula (I) wherein $R_4$ is as defined above.

The condensation or esterification may be effected, for example, by converting the carboxylic acid to an activated derivative such as an acid chloride, for example using $PCl_5$ or thionyl chloride, or by the use of a coupling agent such as dicyclohexylcarbodiimide or its water soluble derivatives such as 3-(3-dimethylaminopropyl)-1-thylcarbodiimide. Alternatively, coupling agents such as 2-(1H-benzotriazol-1-yl)-1,1,3,3-tetramethyluroniumhexafluorophosphate (HBTU) or O-(7-azabenzotriazol-1-yl)-N-N-N',N'-tetramethyluroniumhexafluorophosphate (HATU) may be used.

Compounds of formula (I) in which $R_4$ is —COR can be prepared from corresponding compounds in which $R_4$ is —$CO_2$H by standard functional group interconversions known to those of skill in the art. For example, the carboxylic acid can be converted to a corresponding acyl chloride, for example by reaction with $PCl_5$ or thionyl chloride. The acyl chloride can then be reacted with HMeNOMe, to give Weinreb's amide, which can be reacted with an appropriate nucleophile, for example a Grignard reagent or alkyl or aryl lithium compound to give a compound of formula (I) in which $R_4$ is —COR.

Certain compounds of formula (I) in which $R_4$ is heteroaryl may be conveniently synthesised by the cyclisation of corresponding compounds of formula (I) in which $R_4$ is a thiosemicarbazide moiety. Such cyclisations may be effected by standard methods known to those of skill in the art.

For example, cyclisation of the compounds of formula (I) in which $R_4$ is thiosemicarbazide to corresponding compounds of formula (I) in which $R_4$ is a thiol substituted 1,2,4 triazole group may be effected by reaction with a base such as sodium hydroxide or potassium tert butoxide according to methods described in Czollner L. Arch Pharm. 1990, 323, 221. Alkylation or arylation of the thiol group may be effected by standard techniques, for example with reagents such as benzyl or phenacyl halides in the presence of a base such as triethylamine or sodium carbonate. Further substituted triazoles can be thereby obtained.

Compounds of the formula (I) wherein $R_3$ and $R_4$ together form a phenyl moiety and $R_2$ is aryl or heteroaryl can be prepared according to Scheme 2 set out below.

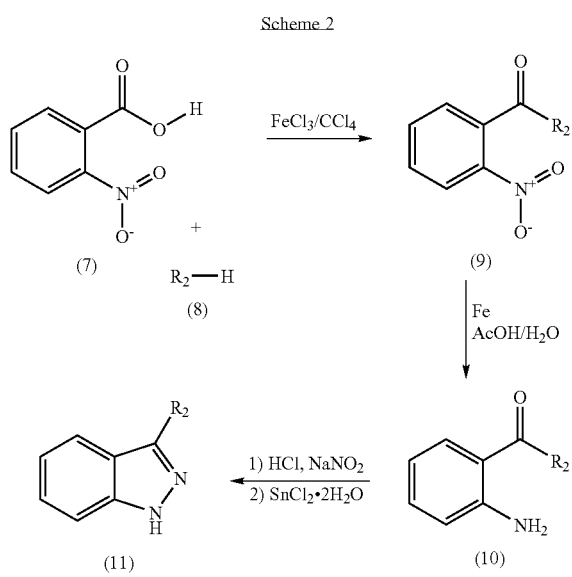

In Scheme 2 above, a Friedel Crafts acylation of a compound of formula (8) may be effected using, for example, a catalyst such as iron (II) chloride. Other catalysts such as titanium tetrachloride, tin (IV) chloride or aluminium chloride may be employed but iron (III) chloride is preferred. Solvents such as dichloromethane, or 1,2-dichloroethane may be used.

A compound of formula (9) may be reduced to a corresponding compound of formula (10) using, for example, iron metal in acetic acid. Tin (II) chloride may also be used. The conversion of a compound of formula (10) to a corresponding compound of formula (11) can be effected by diazotisation using, for example, sodium nitrite and an acid such as hydrochloric acid or sulfuric acid at −5 to 0° C., followed by reduction of the diazo group with tin (II) chloride and resultant cyclisation.

The compounds of formulae (7) and (8) are known compounds, or may be prepared by analogy with known methods.

The Friedel-Crafts reaction between the compounds of formulae (7) and (8) is particularly effective when $R_2$ is aryl, furyl or thiophenyl.

Compounds of the formula (11) wherein $R_2$ is 3- to 6-membered heterocyclyl, $C_3$-$C_6$ carbocyclyl, —XR wherein X and R are as defined in the formula (I), $C_1$-$C_6$ alkyl, $C_2$-$C_6$ alkenyl or $C_2$-$C_6$ alkynyl can be prepared by activating a compound of formula (12)

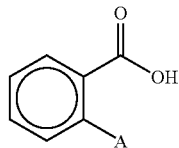

wherein A is a protected amino group, and reacting it with an appropriate nucleophile, followed by cyclisation to form the indazole moiety, The compounds of formula (12) are known compounds or may be prepared by analogy with known methods. They can be activated, for example, by reacting the compound of formula (12) with $PCl_5$, to give an acyl chloride, or with triflic anhydride. The activated compound can then be reacted with an appropriate nucleophile to add the $R_2$ group. Appropriate nucleophiles include Grignard reagents such as $R_2$—MgBr and lithium compounds such as $R_2$-Li. When $R_2$ is a heterocyclyl group an appropriate nucleophile may be $R_2$—H.

Following reaction with a nucleophile, the amino group can be deprotected. Subsequent cyclisation leads to a compound of formula (11) wherein $R_2$ is 3- to 6-membered heterocyclyl, $C_3$-$C_6$ carbocyclyl —XR wherein X and R are as defined in the formula (I), $C_1$-$C_6$ alkyl, $C_2$-$C_6$ alkenyl or $C_2$-$C_6$ alkynyl.

The compounds of formulae (11) and (12) may be alkylated or arylated at the 1-position by reaction with a compound of formula $R_1$-L or Ar—$B(OH)_2$ as described above.

Compounds of formula (I) in which $R_3$ and $R_4$ together form a phenyl group may also be prepared from compounds of formula (13)

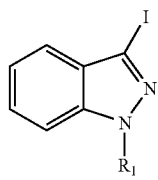

wherein $R_1$ is as defined in the formula (I). Such compounds are known, or may be prepared by analogy with known methods. For example, the synthesis of 3-iodo-1H-indazole is taught in Auwers et al. J. Prakt Chem. 1924, 108, 314. 3-Iodo-1H-indazole may be alkylated or arylated at the 1-position by reaction with a compound of formula $R_1$-L or $ArB(OH)_2$, as described above, to give a compound of formula (13).

Compounds of formula (13) can then be reacted with a compound of formula (14)

$$Me_3Sn—R_2 \qquad (14)$$

wherein $R_2$ is aryl, heteroaryl, —XR wherein X is a divalent $C_2$-$C_6$ alkenyl or $C_2$-$C_6$ alkynyl group and R is as defined above, or $R_2$ is $C_2$-$C_6$ alkenyl or $C_2$-$C_6$ alkynyl. Typically, the reaction takes place in the presence of a palladium catalyst such as palladium tetrakis-triphenylphosphine.

The compounds of formula (14) are known compounds or may be prepared by analogy with known methods. For example, methyl 2-trimethylstannyl-5-furanoate can be prepared by reaction of methyl 5-bromo-2-furanoate with hexamethylditin in a solvent such as 1,2-dimethoxyethane in the presence of a catalyst such as palladium tetrakis-triphenylphosphine.

Compounds of formula (I) where $R_2$ is a substituted oxadiazole may be conveniently prepared according to Scheme (3) below.

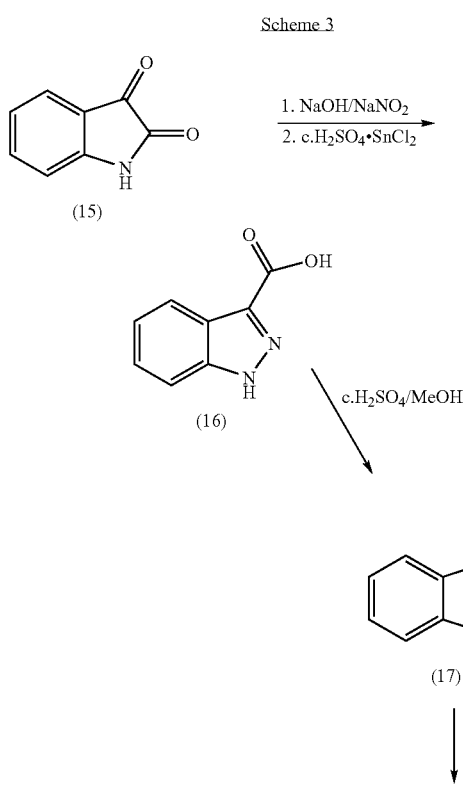

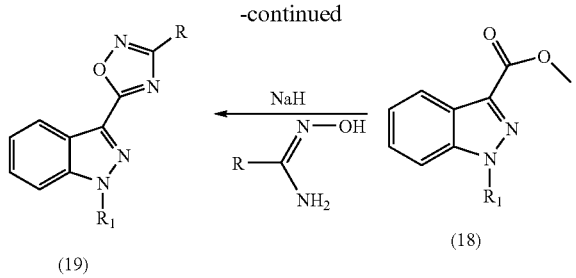

In Scheme (3), the indazole-3-carboxylic acid of formula (16) can be prepared by methods disclosed in von.Auwers & Dereser, Chem.Ber., 1919, 52, 1345. The compound of formula (16) can be esterified using conc. $H_2SO_4$/methanol. Other acids such as hydrochoric acid can also be employed. The compound of formula (17) can be alkylated or arylated by reaction with a compound of formula $R_1$-L or $ArB(OH)_2$ as set out above, to give a compound of formula (18).

Reaction of a compound of formula (18) with a hydroxy amidine in the presence of a base such as sodium hydride can yield the substituted oxadiazoles of formula (19). The substituted hydroxy amidines can be prepared from a nitrile and hydroxylamine in the presence of a base such as sodium methoxide conveniently formed from sodium metal and methanol.

Compounds of formula (I) where $R_2$ is substituted 3-propylamino may conveniently be prepared as shown in Scheme 4 below.

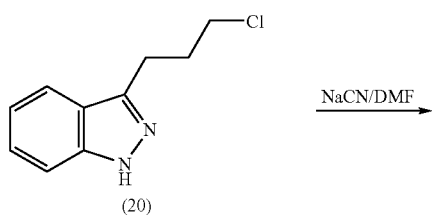

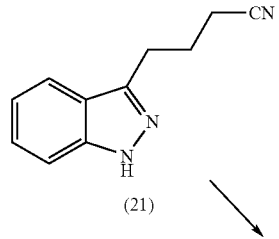

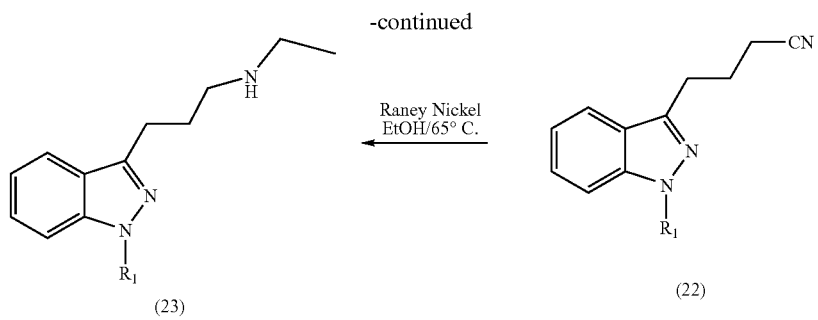

In Scheme 4, the compound of formula (20) can be prepared according to Sasakura et al. Synth, Comm, 1988, 18, 159. The chloride can be converted to the nitrile of formula (21) using sodiun cyanide in DMF at a temperature of 90°. The compound of formula (21) may then be alkylated or arylated with a compound of formula $R_1$-L or ArB(OH), as set out above, to give a compound of formula (22). The compound of formula (22) can then be reduced to a compound of formula (23) using, for example, Raney nickel in ethanol at 65°.

Compounds of formula (I), wherein $R_3$ and $R_4$ together form a phenyl group and $R_2$ is —COR, —CONR'R" or —CO$_2$R' wherein R, R' and R" are as defined in the formula (I), may be prepared by alkylating or arylating indazole 3-carboxylic acid methyl ester, prepared according to von Auwers & Dereser, Chem. Ber, 1919, 52, 1345 with a compound of formula $R_1$-L or ArB(OH)$_2$ as described above. The alkylated or arylated compound can then be hydrolysed to the corresponding carboxylic acid using sodium hydroxide. The carboxylic acid can then be esterified or condensed with an amine of formula HNR'R" by known methods, for example in the presence of a coupling agent such as HATU, TBTU or HBTU.

Compounds of formula (I), wherein $R_3$ and $R_4$ together form a phenyl group and $R_2$ is —COR can be prepared from the corresponding carboxylic acids via Weinreb's amide, as described above.

A compound of formula (I) can be salified by known methods, by contacting the compound with an appropriate acid or base.

The compounds of the invention are capable of inhibiting voltage dependent sodium channels. They can therefore be used, for example, to protect cells against damage which results from overstimulation of sodium channels. Nitric oxide (NO) has recently been implicated in overstimulation of voltage dependent sodium channels. The compounds of the invention can therefore be used to protect cells against NO mediated damage resulting from the overstimulation of voltage dependent sodium channels.

The compounds of the invention are, in particular, effective in protecting neuronal white matter, or myelin coated nerve cell fibres. They therefore have a neuroprotective effect on ganglion cells and axons and can be used in the treatment or prevention of an affective disorder, an anxiety disorder, a behavioural disorder, a cardiovascular disorder, a central or peripheral nervous system degenerative disorder, a central nervous system injury, a cerebral ischaemia, a chemical injury or substance abuse disorder, a cognitive disorder, an eating disorder, an eye disease, Parkinson's disease, pain or a seizure disorder.

Examples of affective disorders which can be treated or prevented with the compounds of the invention include mood disorders, bipolar disorders (both Type 1 and Type II) such as seasonal affective disorder, depression, manic depression, atypical depression and monodepressive disease, schizophrenia, psychotic disorders, mania and paranoia Examples of anxiety disorders which can be treated or prevented with the compounds of the invention include generalised anxiety disorder (GAD), panic disorder, panic disorder with agoraphobia, simple (specific) phobias (e.g. arachnophobia, performance anxiety such as public speaking), social phobias, post-traumatic stress disorder, anxiety associated with depression, and obsessive compulsive disorder (OCD).

Examples of behavioural disorders which can be treated or prevented with the compounds of the invention include behavioural and psychological signs and symptoms of dementia, age-related behavioural disorders, pervasive development disorders such as autism, Aspergers Syndrome, Retts syndrome and disintegrative disorder, attention deficit disorder, aggressivity, impulse control disorders and personality disorder.

Examples of cardiovascular disorders which can be treated or prevented with the compounds of the invention include atherosclerosis, cardiac arrest, thrombosis. complications arising from coronary artery bypass surgery, myocardial infarction, reperfusion injury, intermittant claudication, ischaemic retinopathy, angina, pre-eclampsia, hypertension, congestive cardiac failure, restenosis following angioplasty, sepsis and septic shock.

Examples of central and peripheral nervous system degenerative disorders which can be treated or prevented with the compounds of the invention include corticobasal degeneration, demyelinating disease such as multiple sclerosis and disseminated sclerosis, Freidrich's ataxia, motorneurone diseases such as amyotrophic lateral sclerosis and progressive bulbar atrophy, multiple system atrophy, myclopathy, radiculopathy, peripheral neuropathies such as diabetic neuropathy, tabes dorsalis, drug-induced neuropathy and vitamin deficiency, systemic lupus erythamatosis, granulomatous disease, olivo-ponto-cerebellar atrophy, progressive pallidal atrophy, progressive supranuclear palsy and spasticity.

Examples of central nervous system injuries which can be treated with the compounds of the invention include traumatic brain injury, neurosurgery (surgical trauma), neuroprotection for head injuries, raised intracranial pressure, cerebral oedema, hydrocephalus and spinal cord injury.

Examples of cerebral ischaemias which can be treated or prevented with the compounds of the invention include transient ischaemic attack, stroke, for example thrombotic stroke, ischaemic stroke, embolic stroke, haemorrhagic stroke or lacunar stroke, subarachnoid haemorrhage, cerebral vasospasm, peri-natal asphyxia, drowning, cardiac arrest and subdural haematoma.

Examples of chemical injuries and substance abuse disorders which can be treated or prevented with the compounds of the invention include drug dependence, for example opiate dependence, benzodiazepine addition, amphetamine addiction and cocaine addiction, alcohol dependence, methanol toxicity, carbon monoxide poisoning and butane inhalation.

Examples of cognitive disorders which can be treated or prevented with the compounds of the invention include dementia, Alzheimers Disease, Frontotemporal dementia, multi-infarct dementia, AIDS dementia, dementia associated with Huntingtons Disease, Lewy body Dementia, Senile dementia, age-related memory impairment, cognitive impairment associated with dementia, Korsakoff syndrome and dementia pugilans.

Examples of eating disorders which can be treated or prevented with the compounds of the invention include anorexia nervosa, bulimia, Prader-Willi syndrome and obesity.

Examples of eye diseases which can be treated or prevented with the compounds of the invention include drug-induced optic neuritis, cataract, diabetic neuropathy, ischaemic retinopathy, retinal haemorrhage, retinitis pigmentosa, acute glaucoma, in particular acute normal tension glaucoma, chronic glaucoma, in particular chronic normal tension glaucoma, macular degeneration, retinal artery occlusion and retinitis.

Examples of Parkinson's diseases which can be treated or prevented with the compounds of the invention include drug-induced Parkinsonism, post-encephalitic Parkinsonism, Parkinsonism induced by poisoning (for example MPTP, manganese or carbon monoxide poisoning), Dopa-responsive dystonia-Parkinsonism, post-traumatic Parkinson's disease (punch-drunk syndrome), Parkinson's with on-off syndrome, Parkinson's with freezing (end of dose deterioration) and Parkinson's with prominent dyskinesias.

Examples of pains which can be treated or prevented with the compounds of the invention include acute pain (e.g. musculoskeletal and post-operative pain) and chronic pain such as osteoarthritis, neuropathic pain, cancer pain, trigeminal neuralgia, migraine and other conditions associated with cephalic pain, primary and secondary hyperalgesia, inflammatory pain, nociceptive pain, tabes dorsalis, phantom limb pain, spinal cord in, cry pain, central pain, post-herpetic pain and HIV pain, non-cardiac chest pain, irritable bowel syndrome and pain associated with bowel disorders and dyspepsia.

Examples of seizure disorders which can be treated or prevented with the compounds of the invention include epilepsy and post-traumatic epilepsy, partial epilepsy (simple partial seizures, complex partial seizures, and partial seizures secondarily generalised seizures), generalised seizures, including generalised tonic-clonic seizures (grand mat), absence seizures (petit mal), myoclonic seizures, atonic seizures, clonic seizures, and tonic seizures, Lennox Gastaut, West Syndome (infantile spasms), multiresistant seizures and seizure prophylaxis (anti-epileptogenic).

The compounds of the invention are particularly effective in protecting ganglion cells and axons of the optic nerve from damage. They are therefore particularly effective in the treatment or prevention of glaucoma, for example acute glaucoma or chronic glaucoma. As the compounds of the invention are effective as neuroprotectors for white matter, they can be used specifically in the treatment or prevention of normal tension, or normal pressure, glaucoma Accordingly, when the compounds of the invention are used in the treatment or prevention of glaucoma, they are preferably used in the treatment or prevention of normal tension, or normal pressure, glaucoma As is evident from the discussion above, the compounds of the invention are, of course, also useful in the treatment or prevention of diseases other than glaucoma which are attributable to overstimulation of voltage dependent sodium channels. The said 1-benzyl-3-(furanyl, phenyl, pyrrolyl or thienyl)-indazoles are preferred in this latter regard, as are the said 1-benzyl-3-aryl-indazoles and 1-benzyl-3-heteroaryl-indazoles.

A further preferred use of the compounds of the invention is in the treatment or prevention of multiple sclerosis.

As explained above, certain compounds of the invention are known as activators of soluble guanylate cyclase (sGC). In one embodiment, the present invention provides a compound of formula (I), as defined above, or a pharmaceutically acceptable salt thereof in the manufacture of a medicament for use in blockading voltage dependent sodium channels, wherein the compound of formula (I) or the salt thereof does not activate sGC. Such compounds may have fewer side effects when used to protect neuronal white matter in accordance with the invention.

An enzyme immunoassay to measure changes in cGMP can be conducted to assess the ability of a compound to activate sGC. To perform the assay, recombinant sGC can be added to 1.1 mg/ml IBMX, 2.6 mg/ml GTP, 667 nM DeaNO and the test compound (10 µM). The mixture can then be incubated at room temperature for 10 minutes. Compounds can be formulated in DMSO diluted in Tris HCl (pH 7.4) buffer and with a final DMSO concentration of <0.5%.

To determine the amount of cGMP produced, the Biotrak™ cGMP enzyme immunoassay system commercially available from Amersham™ can be used.

The assay is based on the competitition between unlabelled cGMP and a fixed quantity of peroxidase labelled cGMP for a limited amount of cGMP specific antibody. The peroxidase ligand that is bound to the antibody is immobilised on pre-coated microtitre wells. The amount of labelled cGMP is determind using a one pot stabilised substrate. The concerntration of unlabelled cGMP in a sample is determined by interpolation from a standard curve.

As used herein, a compound which "does not active sGC" typically achieves a cGMP change in the above assay, with 1µM test compound in the absence of a NO donor, of less than 120% of the DEANO response, preferably 100% or less than the DEANO response.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, either subcutaneously, intravenously, intramuscularly, intrastemally, transdermally or by infusion techniques. The compounds may also be administered as suppositories.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugarcoating or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginte, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective amount of a compound of the invention is administered to a patient. A typical daily dose is from about 0.1 to 50 mg per kg of body weight, according to the activity of the specific compound, the age, weight and conditions of the subject to be treated, the type and severity of the disease and the frequency and route of administration. Preferably, daily dosage levels are from 5 mg to 2 g.

Certain compounds of the invention have not previously been disclosed in a therapeutic context Accordingly, the present invention provides a compound of formula (I), as defined above, or a pharmaceutically acceptable salt thereof, for use in the treatment of the human or animal body, excluding:

3-(5'-Hydroxymethyl-2'-furyl)-1-benzylindazole
1-Benzyl-1-3-(5"-methoxycarbonylfuryl)-indazole
1-Benzyl-3-(5"-methoxycarbonyl-2-furyl)-6-methylindazole
1-Benzyl-3-(5"-methoxycarbonyl-2-furyl)-4-6-methoxyindazole
1-Benzyl-3-(5"-methoxycarbonyl-2-furyl)-6-fluoroindazole
1-Benzyl-3-(p-ethoxycarbonylphenyl)indazole
1-Benzyl-3-(5"-hydroxycarbonyl-2-furyl)indazole
1-Benzyl-3-(5"-hydroxycarbonylfuryl-6-methylindazole
1-Benzyl-3-(5"-hydroxycarbonylfuryl)-6-methoxyindazole
1-Benzyl-3-(5"-hydroxycarbonylfuryl)-6-fluoroindazole
1-Benzyl-3-(5"-hydroxycarbonylfuryl)-indazole
1-Benzyl-3-(5"-hydroxymethylfuryl)indazole
1-Benzyl-3-(5"-hydroxymethylfuryl)-methylindazole
1-Benzyl-3-(5"-hydroxymethylfuryl)-6-methoxyidazole
1-Benzyl-3-(5"-hydroxymethylfuryl)-6-fluoroindazole
1-Benzyl-3-(p-hydroxymethylphenyl)indazole
1-(2-Fluorobenzyl)-3-(5-hydroxymethylfuran-2-yl)indazole
1-(2-Methoxybenzyl)-3-(5-hydroxymethylfuran-2-yl)indazole
1-(4Methoxybenzyl-3-(5-hydroxymethylfuran-2-yl)-indazole
3-(5-(1,3-Dioxolan-2-yl)furan-2-yl)indazole
1-(2-Cyanobenzyl)-3-(5-(1,3-dioxolan-2-yl)furan-2-yl)-indazole
1-(2-Cyanobenzyl)-3-(5-formyl-2-furanyl)-indazole
1-(2-Cyanobenzyl)-3-(5-hydroxymethylfuran-2-yl)-indazole
1-Benzyl-3-[5-(1,3-dioxolan-2-yl)-furan-2-yl]-indazole
1-Benzyl-3-(5-formylfuran-2-yl)-indazole
1-[5-(1-Benzylindazole-3-yl)-furan-2-yl]-ethanol
3-(5-Acetylfuran-2-yl)-1-benzyl-indazole
3-(5-Azidomethylfuran-2-yl)-1-benzyl-indazole
3-(5-Aminomethylfuran-2-yl)-1-benzyl-indazole
1-Benzyl-3-(5-nitrofuran-2-yl)-indazole
5-[1-(2-Nitro-benzyl)-1H-indazol-3-yl]-furan-2-carbaldehyde
3-[3-(5-Formyl-furan-2-yl)-indazol-1-ylmethyl]-benzonitrile
5-[1-(4-Fluoro-benzyl)-1H-indazol-3-yl]-furan-2-carbaldehyde
1-(2,4Dichloro-benzyl)-3-(5-[1,3]dioxan-2-yl-furan-2-yl)-1H-indazole
3-(5-[1,3]Dioxan-2-yl-furan-2-yl)-1-(4-fluoro-benzyl)-1H-indazole
Acetic acid 5-(1-benzyl-1H-indazol-3-yl)-furan-2-ylmethyl ester
1-Benzyl-3-[5-(tert-butyl-dimethyl-silanyloxymethyl)-furan-2-yl]-1H-indazole
E-5-(1-Benzyl-1H-indazol-3-yl)furan-2-carbaldehyde oxime
5-(1-Benzyl-6-methoxy-1H-indazol-3-yl)-furan-2-carbaldehyde
Acetic acid 5(1-benzyl-6-methoxy-1H-indazol-3-yl)-furan-2-ylmethyl ester
5-[1-(1,2,4-Dichloro-benzyl)-1-indazol-3-yl]-furan-2-carbaldehyde
5-[1-(3,5-Dimethyl-benzyl)-1H-indazol-3-yl]-furan-2-carbaldehyde
5-(1-Benzyl-1H-indazol-3-yl)thiophene-2-carbaldehyde
5-(1-Benzyl-6-methoxy-1H-indazol-3-yl)-furan-2-carbaldehyde oxime
5-(1-Benzyl-1 H-indazol-3-yl)-furan-2-carbaldehyde oxime
4-[3-(5-Formyl-furan-2-yl)-indazol-1-ylmethyl]-benzonitrile
5-[1-(2-Fluoro-benzyl)-1H-indazol-3-yl]-furan-2-carbaldehyde
1-Benzyl-3-(5-oxiranylmethoxymethyl-furan-2-yl)-1H-indazole
1-Benzyl-3-(5-methoxymethoxymethyl-furan-2-yl)-1H-indazole
5-[1-(3-Methoxy-benzyl)-1H-indazol-3-yl]-furan-2carbaldehyde Preferred compounds for use in the treatment of the human or animal body by therapy arc compounds of formula (I), as defined above, and pharmaceutically acceptable salts thereof, wherein, when $R_1$ is benzyl and $R_3$ and $R_4$, together with the carbon atoms to which they are attached, form a phenyl group, $R_2$ is not furanyl or phenyl. More preferably, $R_2$ is not furanyl, phenyl, pyrrolyl or thienyl. Further preferred compounds for use in the treatment of the human or animal body are compounds of formula (I) in which $R_3$ and $R_4$ do not together form a phenyl group.

Particularly preferred compounds for use in the treatment of the human or animal body by therapy are compounds of formula (I), as defined above, and pharmaceutically acceptable salts thereof wherein, when $R_2$ is a heteroaryl group, it is an oxadiazolyl group. More preferably, $R_2$ is aryl, 3- to 6-membered heterocyclyl, $C_3$-$C_6$ carbocyclyl or —XR wherein X is a divalent $C_1$-$C_6$ alkyl, $C_2$-$C_6$ alkenyl or $C_2$-$C_6$ alkynyl group and R is aryl, heteroaryl, 3- to 6-membered heterocyclyl or $C_3$-$C_6$ carbocyclyl, or $R_2$ is $C_1$-$C_6$ alkyl, $C_2$-$C_6$ alkenyl, $C_2$-$C_6$ alkynyl or —COR, —CONR'R" or —CO$_2$R' wherein each R' and R" is the same or different and is selected from hydrogen, $C_1$-$C_6$ alkyl and aryl and R is selected from $C_1$-$C_6$ or aryl.

Certain compounds of the invention are novel. These compounds are set out in claim 14. Preferred novel compounds are compounds of the formula (I), as defined above, and pharmaceutically acceptable salts thereof, wherein:

(a) when $R_1$ is benzyl and $R_3$ and $R_4$, together with the carbon atoms to which they are attached, form a phenyl group, $R_2$ is not furanyl or phenyl; and (b) when $R_1$ is benzyl t-butyl, methyl or ethyl, $R_2$ is t-butyl, —CONH-phenyl or methyl and $R_3$ is hydrogen, $R_4$ is not —CONHPh, —CONH—NHCOPh, —CONH—NH—CCONHPh, —CONH$_2$, methyl triazolyl, —CONH—NHOtBu or —CONH—NH—CS—NHMe.

More preferably, under the circumstances set out in (a) above, $R_2$ is not furanyl, phenyl, pyrrolyl or thienyl. Further it is preferred that when $R_1$ is benzyl or $C_1$-$C_4$ alkyl, $R_2$ is —CONH-aryl or $C_1$-$C_4$ alkyl and $R_3$ is hydrogen, $R_4$ is not $C_1$-$C_4$ alkyl, heterocyclyl or a substituted or unsubstituted amide moiety.

Particularly preferred novel compounds of the invention are compounds of formula (I) in which $R_3$ and $R_4$, together with the carbon atoms to which they are attached, form a phenyl group (i.e. indazole compounds) and in which $R_1$ and $R_2$ are as defined above, provided that when $R_1$ is benzyl, $R_2$ is not furanyl or phenyl. Of these compounds, compounds in which $R_2$ is not furanyl, phenyl, pyrrolyl or thienyl are more preferred.

The Examples which follow illustrate the invention.

PREPARATION EXAMPLE 1

5-Methoxycarbonyl-2-furyl-2-nitrophenyl ketone

A suspension of 2-nitrobenzoic acid (30.0 g, 0.18 mol) in thionyl chloride (100 mL) with a catalytic amount of N,N-dimethylformamide (50 μL) was heated to reflux for 2 h. After cooling, the excess thionyl chloride was removed under reduced pressure. The residual oil was dissolved in $CH_2Cl_2$ (100 mL) and to this solution was added $FeCl_3$ (0.60 g, 3.70 mmol) portion-wise followed by methyl furanoate (22 mL, 0.21 mol). The resultant mixture was heated to reflux for IS h. A further portion of $FeCl_3$ (0.60 g, 3.70 mmol) was added to the mixture and heating continued for a further 4 h. The mixture was allowed to cool to ambient temperature and then poured onto water (100 mL). The layers were separated and the aqueous layer was extracted with $CH_2Cl_2$ three times. The combined organic material was washed three times with saturated aqueous $NaHCO_3$, dried ($MgSO_4$) and concentrated under reduced pressure. The crude material was initially purified through a plug of silica using a cyclohexane-EtOAc gradient, then the solid was recrystallised from hexane/$CH_2Cl_2$ to provide the product as fine yellow needles (14.97 g, 30%): mp 137-138° C.; MS [EI] (M-OCH$_3$)$^+$244; $^1$H-NMR (CDCl$_3$) 3.90 (s, 3H), 7.24 (m, 2H), 7.61 (dd, 1H, J=7.4, 1.5 Hz), 7.74 (m, 1H), 7.82 (m, 1H), 8.25 (dd, 1H, J=8.1, 1.1 Hz); Anal. ($C_{13}H_9NO_6$) C, calcd 56.73; found 56.48, H, calcd 3.30; found 2.90, N, calcd 5.09; found 4.95.

PREPARATION EXAMPLE 2

5-Methoxycarbonyl-2-furyl-2-aminophenyl ketone

Iron powder (7.7 g, 0.14 mol) was added in three portions to a solution of 5-methoxycarbonyl-2-furyl 2-nitrobenzyl ketone (7.0 g, 25.4 mmol) in acetic acid (500 mL) containing water (15 mL) at a temperature of 90° C. The mixture was then heated to reflux for 5 h, whereupon TLC analysis indicated the reaction to be complete. The excess acetic acid was removed by rotary evaporation under reduced pressure. Water (400 mL) was added to the residue and the mixture was stirred vigorously for 1 h. The mixture was then basified by the addition of concentrated aqueous ammonia solution and the resultant suspension was filtered through celite. The celite 'cake' was washed with water followed with copious amounts of $CH_2Cl_2$. The combined filtrate layers were separated and the aqueous layer extracted five times with $CH_2Cl_2$. The combined organic material was dried (MgSO$_4$) and concentrated under reduced pressure to give a dark orange solid (5.23 g, 84%). This material was used without further purification in subsequent reactions. A small amount was recrystallised (hexane) to give an orange powder for analysis: mp 104-106° C.; MS [EI] (M$^+$) 245; $^1$H-NMR (CDCl$_3$) 3.96 (s, 3H), 6.10 (bs, 2H), 6.74 (m, 2H), 7.18 (d, 1H, J=3.7 Hz), 7.29 (m, 1H), 7.34 (m, 1H), 8.01 (dd, 1H, J=8.1, 1.4 Hz); Anal. ($C_{13}H_{11}NO_4$) C, calcd 63.67; found 63.48, H, calcd 4.52; found 4.40, N, calcd 5.71; found 5.66.

PREPARATION EXAMPLE 3

5-Methoxycarbonyl-2-furyl-2-aminophenyl ketone

To a solution of 5-methoxycarbonyl-2-furyl 2-nitrophenyl ketone (0.54 g, 1.96 mmol) in EtOAc (100 mL) was added SnCl$_2$.2H$_2$O (1.35 g, 5.98 mmol) and the resultant solution was allowed to stir at rt for 48 h. Reaction mixture poured onto 10% aqueous NH$_3$ solution, mixture shaken and then layers separated. The aqueous layer was extracted twice with EtOAc. The combined organic material was dried (MgSO$_4$) and concentrated under reduced pressure. Generally the crude, orange solid (0.54 g) was used without further purification. If the reaction was heated overnight (5/97/61) then a significant amount of the byproduct, 3-(5''-methoxycarbonyl-2'-furyl)benzisoxazole, was formed.

EXAMPLE 1

(5-Methoxycarbonyl-2-furyl)-1H-indazole

Crude 5-Methoxycarbonyl-2-furyl 2-aminobenzyl ketone (0.54 g, 1.96 mmol) was dissolved in conc. HCl (15 mL) and cooled to −10° C. A solution of NaNO$_2$ (0.15 g, 2.17 mmol) in water (2 mL) was added and the mixture stirred for 1 h, maintaining a temperature of −10° C. A solution of tin (II) chloride dihydrate (1.10 g, 4.88 mmol) in conc. HCl (2 mL) was then added followed by a further 1 h of stirring at −10° C. Ice-water (100 mL) was added and the suspension was extracted three times with EtOAc. The combined extracts was washed with water, dried (MgSO$_4$) and concentrated under reduced pressure. The crude product was purified by passage through a silica plug using a gradient of cyclohexane-EtOAc and then recrystallised (acetone/H$_2$O) to give the product as a yellow, fluffy solid (0.38 g, 79%): mp 157-159° C.; MS (EI) M$^+$ 242; $^1$H-NMR (DMSO) 4.00 (s, 3H), 7.31 (d, 1H, J 3.8 Hz), 7.42 (t, 1H, J 7.3 Hz), 7.58 (t, 1H, J 7.9 Hz), 7.61 (d, 1H J 3.8 Hz), 7.76 (d, 1H, J 8.3 Hz), 8.26 (d, 1H, J 8.3 Hz); $^{13}$C-NMR (CDCl$_3$) 51.90, 108.36, 109.89, 119.72, 120.49, 121.66, 122.34, 127.50, 141.04, 143.75, 152.72, 159.20; Anal. ($C_{13}H_{10}N_2O_3$) C, calcd 64.46; found 64.32, H, calcd 4.16; found 4.30, N, calcd 11.56; found 11.13.

EXAMPLE 2

1-Benzyl-3-(5-methoxycarbonyl-2-furyl)-1H-indazole

A solution of 3-(5-methoxycarbonyl-2-furyl)-1H-indazole (2.0 g, 8.3 mmol) and benzyl bromide (2.5 mL, 21.0 mmol) in THF (100 mL) was added dropwise via dropping funnel to a suspension of sodium hydride (60% dispersion in oil: 0.50 g, 12.5 mmol) in THF (200 mL). The resultant mixture was stirred at room temperature for 20 h. The mixture was poured onto brine and the layers separated. The aqueous layer was extracted three times with ether and then the combined organic material was washed with saturated aqueous $NaHCO_3$ solution, dried ($MgSO_4$) and concentrated under reduced pressure. The residue was chromatographed on silica (EtOAc:cyclohexane 1:4) and then the product was recrystallised (EtOAc/hexane) to give a yellow solid: mp 137-138° C.; MS (EI) $M^{3O}$ 332; $^1$H-NMR ($CDCl_3$) 3.97 (s, 3H), 5.67 (s, 2H), 7.03 (d, 1H, J=3.7 Hz), 7.22-7.43 (m, 9H), 8.27 (d, 1H, J=8.1 Hz); Anal. ($C_{20}H_{16}N2O_3$) C, calcd 72.28; found 71.92, H, calcd 4.85; found 4.75, N, calcd 8.43; found 8.39.

EXAMPLE 3

1-Benzyl-3-(5-methoxycarbonyl-2-furyl)-1H-indazole

3-Iodo-1H-indazole was prepared using the method of Auwers et al. *J Prakt. Chem.* 1924, 108, 314: mp 141-142° C., lit. mp 142° C.

To prepare 1-Benzyl-3-iodo-1H-indazole (CFM793), sodium hydride (60% dispersion in mineral oil)(0.36 g, 9.02 mmol) was stirred under nitrogen in anhydrous THF (10 mL) and the soluion was cooled to 0° C. 3-Iodo-1H-indazole (2.0 g, 820 mmol) was dissolved in THF (30 mL) and this solution was syringed into the flask The reaction mixture was kept at 0° C. while benzyl bromide (1.54 g, 9.02 mmol) was syringed slowly into the flask. The reaction mixture was stirred at 0° C. for 30 minutes then it was warmed to room temperature and kept at this temperature for 48 hours. Water (20 mL) was added slowly and then the mixture was poured onto brine. The organic product was extracted using ethyl acetate (3×50 mL). The combined ethyl acetate extracts were dried over $MgSO_4$, filtered and concentrated under reduced presure. The resulting solid was recrystallised from ethanol to give 1.39 g, 52%: mp 54-55° C.; $^1$H NMR (300 MHz, $CDCl_3$) δ7.42-7.40 (m, 2H), 7.33-7.09 (m, 7H), 5.53 (s, 2H); MS (EI) m/z 334 [M⁺]; Anal. $C_{14}H_{11}N_2I$ calculated C, 50.31; H, 3.29; N, 8.39; found C, 51.05,; H, 3.25; N, 8.00.

A solution of methyl 5-bromofuranoate (0.75 g, 3.66 mmol), hexamethylditin (1.0 g, 3.05 mmol) and Pd(PPh₃)₄ (90 mg, 0.078 mmol) in DME (50 mL) was heated to reflux overnight. The initial amber coloured solution became black The solution was allowed to cool and then filtered and concentrated under reduced pressure. The crude stannane was purified by passage through a plug of silica (1:9 EtOAc: cyclohexane) to give methyl 2-trimethylstannyl-5-furanoate (0.17 g, 19%): $^1$H-NMR ($CDCl_3$); The low yield of the product may be due to its suspected volatility. Pd(PPh₃), (9 mg, 0.008 mmol) was added to a solution of 1-benzyl-3-iodo-1H-indazole (0.13 g, 0.39 mmol) and methyl 2-trimethylstannyl-5-furanoate (0.17 g, 0.588 mmol) in DME (20 mL) and the mixture was heated to reflux overnight. The reaction mixture was allowed to cool to rt, filtered and concentrated under reduced pressure. Purification of the residue by chromatography on silica (3:7 EtOAc:cyclohexane) gave the product as a slightly contaminated yellow solid (88.6 mg, 69%).

EXAMPLE 4

1-Benzyl-3-(5-hydroxymethyl-2-furyl)-1H-indazole

A solution of 1-benzyl-3-(5-methoxycarbonyl-2- yl)-1H-indazole in THF (150 mL) was added dropwise to a suspension of $CaBH_4$.2TBF (3.9 g, 18.23 mmol) in THF (150 mL) at room temperature. The resultant mixture was heated to reflux for 15 h. The reaction mixture was allowed to cool, then poured slowly onto brine.

The layers were separated and the aqueous layer was extracted three times with ether.

The combined organic material was dried ($MgSO_4$) and concentrated under reduced pressure. The crude product was chromatogaphed on silica (30-40% EtOAc/cyclohexane) and then recrystallised (ethanol/$H_2O$) to give the product as fine cream needles (1.56 g, 86%): mp 112-112.55° C. (lit. mp 108-109° C.); MS (EI) M⁺ 304; $^1$H-NMR ($CDCl_3$) 4.76 (s, 2H), 5.68 (s, 2H), 6.50 (d, 1H, J=3.3 Hz), 6.90 (d, 1H, J=3.3 Hz), 7.21-7.40 (m, 8H), 8.08 (d, 1H, J=8.5 Hz); $^{13}$C-NMR ($CDCl_3$) 54.12, 58.53, 108.87, 110.57, 110.59, 122.25, 122.38, 122.50, 127.83, 128.00 (2C), 128.72, 129.68(2C), 137.14, 137.53, 141.45, 149.52, 154.88; Anal. ($C_{19}H_{16}N_2O_2$) C, calcd 74.98; found 74.80, H, calcd 5.30; found 5.28, N, calcd 9.20; found 9.15.

EXAMPLE 5

1-Benzyl-3-(5-hydroxycarbonyl-2-furyl)-1H-indazole

A mixture of 1-benzyl-3-(5-methoxycarbonyl-2-furyl)-1H-indazole (1.46 g, 4.39 mmol), 15% aqueous KOH solution (100 mL) and methanol (100 mL) was heated to reflux for 4 h. The resultant solution was allowed to cool and then diluted with $H_2O$ (300 mL). The solution was acidified to pH 2 by the addition of conc. HCl and the precipitate collected by vacuum filtration. The off-white solid was washed with $H_2O$ and air dried. Recrystallisation of the crude solid (EtOH) gave the product as fine off-white needles (1.16 g, 83%): mp 205-206.5° C. (lit mp 200-202° C.); $^1$H-NMR (DMSO) 5.34 (s, 2H), 6.67 (d, 1H, J 3.6 Hz), 6.89-7.00 (m, 7H), 7.08 (m, 2H), 7.89 (d, 1H, J 8.0 Hz); $^{13}$C-NMR ($CDCl_3$) 52.55, 109.06, 110.91, 119.84, 120.91, 121.22, 122.57, 127.49, 127.69 (2C), 128.02, 128.99(2C), 134.69, 137.40, 140.72, 144.41, 151.75, 159.67; MS (EI) M⁺; Anal. ($C_{19}H_{14}N_2O_3$) C, calcd 73.19; found 73.18, H, calcd 7.17; found 7.16, N, calcd 14.23; found 14.13.

EXAMPLE 6

1-Benzyl-3-(5-hydroxylaminocarbonyl-2-furyl)-1H-indazole

A mixture of 1-benzyl-3-(5-hydroxycarbonyl-2-furyl)-1H-indazole (0.40 g, 1.257 mmol), DMF (cat., 2 drops) and $SOCl_2$ (5 mL) was heated to reflux for 2 h. After cooling, the excess $SOCl_2$ was removed under reduced pressure and the almost black oil was dissolved in DME (8 mL). A portion of this acid chloride solution (2 mL, approx. 0.314 mmol) was mixed with a solution of $NH_2OH.HCl$ (0.20 g, 2.88 mmol) and $K_2CO_3$ (excess) in $H_2O$ (2 mL) and allowed to stir at rt overnight A precipitate formed while stirring. The reaction mixture was poured onto water (50 mL) and extracted four times with EtOAc. The combined organic material was dried ($MgSO_4$) and concentrated under reduced pressure to give the crude product (77.4 mg, 74%) as an orange/brown solid.

EXAMPLE 7

1-Benzyl-3-(5-hydroxylaminocarbonyl-2-furyl)-1H-indazole

To a solution of 1-benzyl-3-(5-hydroxycarbonyl-2-furyl)-1H-indazole (0.20 g, 0.63 mmol) and O-benzotriazol-1-yl-N, N,N',N'-tetramethyluronium tetrafluoroborate (TBTU)(0.21 g, 0.65 mmol) in anhydrous DMF (3 mL) was added N-methylpiperidine (1.4 mL) dropwise at rt. Stirring was continued for 15 min and then NH$_2$OH.HCl (44 mg, 0.63 mmol) was added as a solid. The mixture was stirred at rt overnight Excess DMF was removed by rotary evaporator under high vacuum. The residue was dissolved in EtOAc and washed with a saturated aqueous solution of NaHCO$_3$, H$_2$O, 10% aqueous HCl solution, H$_2$O, dried (MgSO$_4$) and concentrated under reduced pressure. The crude solid was recrystallised (EtOH/H$_2$O) to give the product (0.118 g, 56%): mp 138 (dec.); $^1$H-NMR (DMSO) 5.75 (s, 2H), 7.13 (d, 1H, J 3.4 Hz), 7.23-7.35 (m, 7 H), 7.48 (t, 1H, J 7.7 Hz), 7.79 (d, 1H, J 8.7 Hz), 8.30 (d, 1H, J 7.9 Hz), 9.18 (b, 1H), 11.27 (b, 1H); $^{13}$C-NMR (DMSO); MS (EI) M$^+$ 333; Anal. (C$_{19}$H$_{15}$N$_3$O$_3$.H$_2$O) C, calcd 64.95; found 65.07, H, calcd 4.88; found 4.73, N, calcd 11.96; found 11.83.

EXAMPLE 8

5-(1-Benzyl-1H-indazol-3-yl)-furan-2-carboxylic acid benzyl-hydroxy-amide and 5-(1-Benzyl-1H-indazol-3-yl)-furan-2carboxylic acid N-benzylhydroxylamine ester.

To the acid 1 mL of a [(159.0 mg, 0.5 mmol) in acetonitrile (5 mL)] solution was added the O-(azabenzotriazol-1-yl)-N,N,N',N'-tetramethyluronium dexafluorophosphate 1 mL of a [(190.1 mg, 0.5 mmol in acetonitrile (5 mL)] solution and the diisopropylethylamine resin (0.3 mmol, ~100 mg) followed by the N-benzylhydroxylamine hydrochloride (16 mg, 0.1 mmol). The reaction was heated to 50° for 4 h. The reaction was allowed to cool and filtered. Tetrafluorophthalic anhydride (66 mg, 0.3 mmol) added and the reaction shaken overnight. Water (1 drop) was added and the reaction shaken for 1 h. Tetraalkylammonium polystyrene resin, PS-carbonate, Argonaut Technologies, (500 mg, ~1.5 mmol) was added and the mixture shaken for 24 h. The resin was filtered off and the solvent removed on the rotary evaporator 31.1 mg. LCMS (C18 column, 0.1% trifluoroacetic acid, acetonitrile/H$_2$O) electrospray. m/z 423.42 at 1.69 min and m/z 424 at 3.58 min.

EXAMPLES 9 TO 45

The following compounds were prepared by the technique set out in Example 8. Synthesis was confirmed by LCMS data.

| Example | Compound |
|---|---|
| 9 | 2-Benzyl-5-tert-butyl-2H-pyrazole-3-carboxylic acid phenylamide |
| 10 | 2-Benzyl-5-tert-butyl-2H-pyrazole-3-carboxylic acid benzylamide |
| 11 | 1-(4-Chloro-phenyl)-5-phenyl-1H-pyrazole-3-carboxylic acid phenylamide |
| 12 | 5-tert-Butyl-2-(2,4-dichloro-benzyl)-2H-pyrazole-3-carboxylic acid (4-methoxy-phenyl)-amide |
| 13 | 2-Ethyl-5-thiophen-2-yl-2H-pyrazole-3-carboxylic acid (4-chloro-phenyl)-amide |
| 14 | (S)-5-tert-Butyl-2-(2,4-dichloro-benzyl)-2H-pyrazole-3-carboxylic acid (4-chloro-phenyl)-amide |
| 15 | 5-tert-Butyl-2-(2,4-dichloro-benzyl)-2H-pyrazole-3-carboxylic acid phenethyl-amide |
| 16 | (S)-2-Ethyl-5-thiophen-2-yl-2H-pyrazole-3-carboxylic acid phenethyl-amide |
| 17 | 5-tert-Butyl-2-(2,4-dichloro-benzyl)-2H-pyrazole-3-carboxylic acid phenylamide |
| 18 | 5-tert-Butyl-2-(2,4-dichloro-benzyl)-2H-pyrazole-3-carboxylic acid benzylamide |
| 19 | 1-(4-Chloro-phenyl)-5-phenyl-1H-pyrazole-3-carboxylic acid (4-dimethylamino-phenyl)-amide |
| 20 | 1-(4-Chloro-phenyl)-5-phenyl-1H-pyrazole-3-carboxylic acid (4-tert-butyl-phenyl)-amide |
| 21 | 2-tert-Butyl-5-methyl-2H-pyrazole-3-carboxylic acid (4-tert-butyl-phenyl)-amide |
| 22 | 2-tert-Butyl-5-methyl-2H-pyrazole-3-carboxylic acid (3,4-dichloro-phenyl)-amide |
| 23 | 5-tert-Butyl-2-methyl-2H-pyrazole-3-carboxylic acid (3,4-dichloro-phenyl)-amide |
| 24 | 2-Benzyl-5-tert-butyl-2H-pyrazole-3-carboxylic acid (3,4-dichloro-phenyl)-amide |
| 25 | 2-Benzyl-5-tert-butyl-2H-pyrazole-3-carboxylic acid (4-tert-butyl-phenyl)-amide |
| 26 | 5-tert-Butyl-2-methyl-2H-pyrazole-3-carboxylic acid (4-tert-butyl-phenyl)-amide |
| 27 | 2-Benzyl-5-tert-butyl-2H-pyrazole-3-carboxylic acid (4-dimethylamino-phenyl)-amide |
| 28 | 2-Benzyl-5-tert-butyl-2H-pyrazole-3-carboxylic acid (3-oxazol-5-yl-phenyl)-amide |
| 29 | 5-tert-Butyl-2-methyl-2H-pyrazole-3-carboxylic acid (3-oxazol-5-yl-phenyl)-amide |
| 30 | 1-(4-Chloro-phenyl)-5-phenyl-1H-pyrazole-3-carboxylic acid (5-tert-butyl-isoxazol-3-yl)-amide |
| 31 | 2-tert-Butyl-5-methyl-2H-pyrazole-3-carboxylic acid (4-phenylcarbamoyl-phenyl)-amide |
| 32 | 2-Benzyl-5-tert-butyl-2H-pyrazole-3-carboxylic acid (3-phenylcarbamoyl-phenyl)-amide |
| 33 | 5-tert-Butyl-2-methyl-2H-pyrazole-3-carboxylic acid (3-phenylcarbamoyl-phenyl)-amide |
| 34 | 2-Benzyl-5-tert-butyl-2H-pyrazole-3-carboxylic acid (6-chloro-pyridin-3-yl)-amide |
| 35 | 1-tert-Butyl-5-methyl-1H-pyrazole-3-carboxylic acid (6-chloro-pyridin-3-yl)-amide |
| 36 | 1-tert-Butyl-5-methyl-1H-pyrazole-3-carboxylic acid (4-acetylamino-phenyl)-amide |
| 37 | 1-tert-Butyl-5-methyl-1H-pyrazole-3-carboxylic acid (3-benzyloxy-pyridin-2-yl)-amide |
| 38 | 5-Methyl-1-(4-methyl-benzyl)-1H-pyrazole-3-carboxylic acid (4-acetylamino-phenyl)-amide |
| 39 | 5-tert-Butyl-2-(2,4-dichloro-benzyl)-2H-pyrazole-3-carboxylic acid (4-acetylamino-phenyl)-amide |
| 40 | 2-Ethyl-5-thiophen-2-yl-2H-pyrazole-3-carboxylic acid (4-acetylamino-phenyl)-amide |
| 41 | 5-tert-Butyl-2-(2,4-dichloro-benzyl)-2H-pyrazole-3-carboxylic acid (4-(pyridin-3-yl) thiazol-2-yl)-amide |
| 42 | 2-Ethyl-5-thiophen-2-yl-2H-pyrazole-3-carboxylic acid (4-(pyridin-3-yl) thiazol-2-yl)-amide |
| 43 | 2-Benzyl-5-tert-butyl-2H-pyrazole-3-carboxylic acid (4-acetylamino-phenyl)-amide |
| 44 | 5-tert-Butyl-2-methyl-2H-pyrazole-3-carboxylic acid (4-(pyridin-3-yl) thiazol-2-yl)-amide |
| 45 | 5-tert-Butyl-2-methyl-2H-pyrazole-3-carboxylic acid [3-(4-methoxy-benzyl)-[1,2,4]oxadiazol-5-yl]-amide |

EXAMPLE 46

[N-Ethyl-(4-Aminobutyl)]-1-benzylindazole

A solution of (3-chloropropyl)indazole (Sasakura et al, Synth. Comm., 18, pg 259 (1988))(750 mg, 3.75 mM) in dimethylformamide (25 ml) was stirred at room temperature and sodium cyanide (370 mg, 7.5 mM) added in one portion. The resulting mixture was heated at 90° C. for 4 hr. The dimethylformamide was removed in vacuo and the residue partitioned between water and ethyl acetate. The combined organics were dried over magnesium sulfate. Column chromatography (ethyl acetate/cyclohexane, 1:1) provided 3-(3-cyanopropyl)indazole as a clear oil (3.21 g, 83%).

¹NMR (300 MHz, CDCl₃) 7.75 (1H, d, J 8Hz), 7.40-7.50 (2H, m), 7.20 (1H, t, J 8 Hz), 3.18 (2H, t, J 6 Hz), 2.58 (2H, t, J 6 Hz), 2.20-2.30 (2H, m). M/z=187 (CI).

A solution of this compound (187 mg, 1 mM) in dry tetrahydrofuran (5 ml) was added dropwise to a suspension of sodium hydride (60% in oil, 45 mg, 1.1 mM) in dry tetrahydrofuran (10 ml) at 0° C. After 10 min benzyl bromide (0.13 ml, 188 mg, 1.1 mM) was added and the mixture stirred at 0° C. for 30 min then allowed to warm to room temperature and left stirring overnight. Water (2 ml) was added and the tetrahydrouran removed in vacuo. The residue was partitioned between water and ethyl acetate and the combined organics dried over magnesium sulfate and evaporated. Column chromatography (ethyl acetate/cyclohexane, 1:4) provided 1-benzyl-3-(3-cyanopropyl)indazole as a thick yellow oil (180 mg, 63%). %).

¹NMR (300 MHz, CDCl₃) 7.70 (1H, d, J 8 Hz), 7.10-7.40 (8H, m), 3.15 (2H, t, J 6 Hz), 2.58 (2H, t, J 6 Hz), 2.20-2.30 (2H, m).

A solution of 1-benzyl-3-(3-cyanopropyl)indazole (100 mg, 0.35 mM) in ethanol (10 ml) was stirred at room temperature and Raney nickel (approx. 100 mg, wet weight) was added. The resulting suspension was warmed to 65° C. and hydrazine hydrate (0.1 ml, 87 mg) added carefully. The mixture was stirred at 70° C. for a further 2 hr then cooled and filtered through celite. Solvent was removed in vacuo and the residue purified by chromatography on silica (chloroform/methanol 9:1) to give the title product as a clear oil (25 mg, 26%).

¹NMR (300 MHz, CDCl₃) 7.60 (1H, d, J 8HZ), 6.95-7.25 (8H, m), 5.45 (2H, s), 2.92 (2H, t, J 6 Hz), 2.50-2.60 (4H, t, J 6 Hz), 2.15 (1H, bs), 1.75 (2H, m), 1.55 (2H, m), 1.00 (3H, t, J 6 Hz). M/z=307 (EI). Found C, 74.73; H, 8.16; N, 12.80; $C_{20}H_{25}N_3$ 0.8 $H_2O$ requires: C, 74.67; H, 8.28; N, 13.07.

EXAMPLE 47

1-Benzyl-3-[N-(2-N,N-dimethylaminoethyl)carboxamido]indazole

To a suspension of sodium hydride (60% in oil, 55 mg, 1.22 mM) in dry THF (10 ml) stirring at 0° C. was added a solution of methyl indazole-3-carboxylate (von Auwers et al, *Ber.*, 52, pg 1345 (1919), 210 mg, 1.22 mM) in dry THF (10 ml). After 10 min benzyl bromide (0.15 ml, 1.22 mM) was added and the solution left stirring at room temperature overnight. Water (2 ml) was added and the solvent removed in vacuo. The residue was partitioned between water and ethyl acetate and the combined organic dried over magnesium sulfate and evaporated. Column chromatography (ethyl acetate/cyclohexane 1:4) provided methyl 1 benzyl-indazole-3-carboxylate as a yellow powder (250 mg, 77%). M.pt. 181° C.

¹NMR (300 MHz, CDCl₃) 8.15 (1H, d, J 8 Hz), 7.10-7.30 (8H, m), 5.60 (2H, s), 3.95 (3H, s). M/z=266 (EI). Found C, 72.17; H, 5.20; N. 10.50; $C_{16}H_{14}N_2O_2$ requires: C, 72.18; H, 5.26; N, 10.53.

A suspension of methyl 1-benzyl-indazole-3-carboxylate (400 mg, 1.5 mM) in sodium hydroxide (1N, 10 ml) was heated at 80° C. for 2 hr to give a clear solution. The cooled solution was washed with ethyl acetate then the aquous layer adjusted to pH 5 with 1N hydrochloric acid. 1-Benzyl indazole-3-carboxylic acid was extracted into ethyl acetate, dried over magnesium sulfate, then evaporated to give a white powder (310 mg, 82%). M.pt. 169-171° C.

¹NMR (300 MHz, CDCl₃) 8.28 (1H, d, J 8 Hz), 7.20-7.50 (8H, m), 5.70 (2H, s). M/z=252 (EI). Found C, 70.80; H. 4.71; N, 10.91; $C_{15}H_{12}N_2O_2$ requires: C, 71.43; H, 4.76; N, 11.11.

A solution of 1-benzyl indazole-3-carboxylic acid (25.2 mg, 0.1 mM) in acetonitrile (10 ml) was stirred and HATU (38 mg, 0.1 mM) added. DIPEA resin (0.3 mM, 80 mg) was added followed by N,N dimethylethylenediamine (8.8 mg, 0.1 mM). The resulting mixture was heated at 50° C. for 5 hr. Tetrafluorophthallic anhydride (66 mg, 0.3 mM) was added and the mixture stirred for a further 24 hr. Carbonate resin (630 mg, 2.0 mM) was added and stirring continued for 48 hr and the mixture was then filtered through a short silica column to give, after evaporation in vacuo, the title compound as a thick oil (17 mg, 53%).

¹NMR (300 MHz, CDCl₃) 8.50 (1H, d, J 8 Hz), 7.20-7.50 (8H, m), 5.70 (2H, s), 3.70 (2H, m), 2.68 (2H, m), 2.40 (6H, s). M/z=323 (EI+ve, LC/MS in TFA). Found C, 70.65; H, 6.98; N, 17.16; $C_{19}H_{22}N_4O_2$ requires: C, 70.81; H, 6.83; N, 17.39.

EXAMPLE 48

Indazole-3-carboxylic acid

Isatin (10 g, 0.067 mol) was added to a solution of NaOH (2.8 g, 0.07 mol) in $H_2O$ (44 mL) at 50° C. The stirred clear solution was cooled to 0° C. and a solution of sodium nitrite (4.69 g, 0.067 mol) in $H_2O$ (17 mL) was added and stirring continued. A solution of concentrated $H_2SO_4$ (12.9 g) in $H_2O$ (136 mL) was cooled to 0° C. and added dropwise to the reaction mixture in such a way that the dropper was below the level of the reaction mixture. Stirring was continued for 15 min and a cooled solution of tin(II) chloride dihydrate (36.7 g, 0.16 mol) in concentrated HCl (58 mL) was added over 20 min. The reaction mixture was stirred for 1 h and the orange solid was filtered then heated in $H_2O$ at 100° C. The insoluble solids were removed by filtration and the product crystallised from the solution affording the title compound as a yellow solid (3.4 g, 31%). Mp 261-263° C. d, lit 260-261° C. v.Auwers, Dereser *Chem. Ber.* 1919, 52, 1343. ¹H NMR (300 MHz, DMSO-d₆) ppm 7.26-7.31 (m, 1H), 7.40-7.46 (m, 1H), 7.63-7.66 (m, 1H), 8.08-8.10 (m, 1H), 12.95 (s, 1H), 13.80 (s, 1H). MS(EI) m/z 162 [M⁺].

EXAMPLE 49

Indazole-3-carboxylic Acid Methyl ester

Concentrated $H_2SO_4$ (1 mL) was added to a solution of indazole-3-carboxylic acid (2.0 g, 12 mmol) in MeOH (40 mL). The reaction mixture was heated at reflux for 3 h, the MeOH was removed under reduced pressure and the residue was partitioned between diethyl ether (100 mL) and $H_2O$ (100 mL). Saturated sodium hydrogen carbonate solution was added (100 mL) and the diethyl ether layer was separated. The aqueous layer was further extracted with 2×200 mL of diethyl ether. The combined extracts were dried (MgSO₄) and solvent removed under reduced pressure and the solid was recrystallised from cyclohexane/ethyl acetate to afford the title compound (1.29 g, 61%). Mp 158-159° C., lit 168-169° C. v.Auwers, Dereser *Chem. Ber.* 1919, 52, 1343. ¹H-NMR (300 MHz, CDCl₃) ppm 4.09 (s, 3H), 7.33-7.38 (m, 1H), 7.46-7.52 (m, 1H), 7.71-7.74 (m, 1H), 8.23-8.26 (m, 1H), 12.03 (s, 1H). MS(EI) m/z 176 [M⁺].

EXAMPLE 50

1-Benzylindazole-3-carboxylic acid methyl ester

Sodium hydride (0.37 g. 60%, 9.3 mmol) was added to a solution of indazole-3-carboxylic acid methyl ester (1.5 g, 8.5 mmol) in dry THF (50 mL) at 0° C. Benzyl bromide (1.59 g, 9.3 mmol) was then added and the reaction mixture was warmed to 25° C. and stirred for 8 h The reaction mixture was poured onto saturated NaCl solution (100 mL) and extracted with 3×200 mL of diethyl ether. The combined extracts were dried ($MgSO_4$) and concentrated under reduced pressure. The crude compound was purified by flash chromatography using cyclohexane/ethyl acetate (70:30) and recrystallised from cyclohexane/ethyl acetate to afford the title compound as a yellow solid (1.89 g, 84%). Mp 72-73° C. $^1$H NMR (300 MHz, $CDCl_3$) ppm 4.07 (s, 3H), 5.72 (s, 2H), 7.22-7.40 (m, 8H), 8.24-8.27 (m, 1H). MS(EI) m/z 266 [M+]. Anal. Calcd. for $C_{16}H_{14}N_2O_2$: C, 72.17; H, 5.30; N, 10.52. Found: C, 72.12; H, 5.15; N, 10.85.

EXAMPLE 51

1-Benzyl-3-[3-aminomethyl-1,2,4-oxadiazol-yl]indazole

A solution of aminoacetonitrile hydrochloride (0.5 g, 5.4 mmol) and sodium (0.124 g, 5.4 mmol) in MeOH (15 mL) was added to a solution of hydroxylamine hydrochloride (0.37 g, 5.4 mmol) and sodium (0.124 g, 5.4 mmol) in MEOH. The reaction mixture was refluxed for 4 h then filtered and concentrated under reduced pressure. The crude material was taken up in dry THF (30 mL), sodium hydride (0.114 g, 60%, 2.86 mmol) was added and the reaction mixture heated at 60° C. 1-Benzylindazole-3carboxylic acid methyl ester (0.25 g, 0.938 mmol) was added and the reaction mixture was heated at reflux for 4 h. The THF was removed under reduced pressure and the residue partitioned between chloroform (100 mL) and $H_2O$ (100 mL). The chloroform layer was separated and the aqueous layer was further extracted with 2×100 mL of chloroform. The combined extracts were dried ($MgSO_4$) and concentrated under reduced pressure. The crude compound was purified by flash chromatography using chloroform/MeOH (95:5) to afford the title compound as a white solid (0.264 g, 92%). Mp 118-119° C. $^1$H NMR (300 MHz, $CDCl_3$) ppm 1.68 (s, 2H), 4.12 (s, 2H), 5.77 (s, 2H), 7.30-7.47 (m, 8H), 8.32-8.35 (m, 1H). MS(EI) m/z 305 [M+]. Anal. Calcd. for $C_{17}H_{15}N_5O$: C, 66.87; H, 4.95; N, 22.94. Found: C, 67.00; H. 4.82; N, 22.97.

EXAMPLE 52

1-Benzyl-3-[3-(N,N-dimethylaminomethyl)-1,2,4oxadiazol-5-yl]indazole

Hydroxylamine hydrochloride (124 g 17.8 mmol) was added to a solution of sodium (0.64 g, 26 mmol) in MeOH (100 mL). The reaction mixture was stirred at 25° C. for 15 min then dimethylaminoacetonitrile (1.5 g, 17.8 mmol) in MeOH (5 mL) was added and the reaction mixture stirred at 25° C. for a further 5 days. The solid was removed by filtration and the liquid concentrated under reduced pressure. The crude material was taken up in dry THF (100 mL) and sodium hydride (0.114 g, 60%, 2.86 mmol) was added and the reaction mixture was heated to 50° C. 1-Benzylindazole-3-carboxylic acid methyl ester (0.25 g, 0.938 mmol) was added and the reaction mixture was heated at reflux for 4 h. The THF was removed under reduced pressure and the residue partitioned between chloroform (100 mL) and $H_2O$ (100 mL). The chloroform layer was separated and the aqueous layer was further extracted with 2×100 mL of chloroform. The combined extracts were dried ($MgSO_4$) and concentrated under reduced pressure. The crude compound was purified by flash chromatography using chloroform/MeOH (97.5:2.5) to afford the title compound (0.151 g, 48%) as a yellow solid. Mp 93-95° C. $^1$H NMR (300 MHz, $CDCl_3$) ppm 2.40 (s, 6H), 3.77 (s, 2H), 5.68 (s, 2H), 7.19-7.37 (m, 8H), 8.27-8.30 (m, 211). MS(FAB) m/z 334 [M+H]+. HRMS Calcd. for $C_{19}H_{20}N_5O$: 334.1668. Found: 334.1655 [M+H]+.

EXAMPLE 53

Biological Assay

The effectiveness of the compounds of the present invention as sodium channel blockers were investigated in an assay measuring how they inhibit the flux of [$^{14}$C]-labelled guanidine through sodium channels, as described in Pauwels, P. J., Leysen, J. E., Laduron, P. M. [$^3$H]Batrachotoxinin A 20-α-benzoate binding to sodium channels in rat brain: characterization and pharmacological significance. *Eur. J. Pharmacol.*, 1986, 124, 291-298. The data is presented below in Table 1, expressed as $IC_{50}$ values in μM.

TABLE 1

| Compound | Example No | Guanidine Flux |
|---|---|---|
| 1-Benzyl-3-(5-hydroxymethyl-2-furyl)-1H-indazole | 4 | 17 |
| 1-Benzyl-3-(5-methoxycarbonyl-2-furyl)-1H-indazole | 3 | 15.5 |
| 1-Benzyl-3-[3-aminomethyl-1,2,4-oxadiazol-5-yl]indazole | 51 | 22.4 |
| 1-Benzyl-3-(5-hydroxylaminocarbonyl-2-furyl)-1H-indazole | 6 | 30.9 |
| 1-Benzyl-3[3-(N,N-dimethylaminomethyl)-1,2,4-oxadiazol-5-yl]indazole | 52 | 33.9 |
| 2-Benzyl-5-tert-butyl-2H-pyrazole-3-carboxylic acid N'-(3-chlorophenylcarbamoyl) hydrazide | | 5.8 |
| 2-{5-[5-tert-Butyl-2-(4-fluoro-benzyl)-2H-pyrazol-3-yl]-4-methyl-4H-[1,2,4]triazol-3-ylsulfanyl}-1-(4-chloro-phenyl)-ethanone | | 4.6 |
| 3-Benzylsulfanyl-5-[5-tert-butyl-2-(4-fluoro-benzyl)-2H-pyrazol-3-yl]-4-methyl-4H-[1,2,4]triazole | | 12.3 |
| 2-Benzyl-5-tert-butyl-2H-pyrazole-3-carboxylic acid (4-chloro-phenyl)-amide | | 4.4 |
| [N-Ethyl-(4-Aminobutyl)]-1-benzylindazole | 46 | 15.5 |
| 1-Benzyl-3-[N-(2-N,N-dimethylaminoethyl) carboxamido]indazole | 47 | 63.01 |
| 5-(1-Benzyl-1H-indazol-3-yl)-furan-2-carboxylic acid benzyl-hydroxy-amide AND 5-(1-benzyl-IH-indazol-3-yl)-furan-2-carboxylic acid N-benzylhydroxylamine ester | 8 | 3.9 |
| 2-Benzyl-5-tert-butyl-2H-pyrazole-3-carboxylic acid phenylamide | 9 | <9 |
| 2-Benzyl-5-tert-butyl-2H-pyrazole-3-carboxylic acid benzylamide | 10 | 7 |
| 1-(4-Chloro-phenyl)-5-phenyl-1H-pyrazole-3-carboxylic acid phenylamide | 11 | 18 |
| 5-tert-Butyl-2-(2,4-dichloro-benzyl)-2H-pyrazole-3-carboxylic acid (4-methoxy-phenyl)-amide | 12 | <9 |
| 2-Ethyl-5-thiophen-2-yl-2H-pyrazole-3-carboxylic acid (4-chloro-phenyl)-amide | 13 | 17 |
| (S)-5-tert-Butyl-2-(2,4-dichloro-benzyl)-2H-pyrazole-3-carboxylic acid (4-chloro-phenyl)-amide | 14 | 29 |
| 5-tert-Butyl-2-(2,4-dichloro-benzyl)-2H-pyrazole-3-carboxylic acid phenethyl-amide | 15 | 10 |
| (S)-2-Ethyl-5-thiophen-2-yl-2H-pyrazole-3-carboxylic acid phenethyl-amide | 16 | 13 |
| 5-tert-Butyl-2-(2,4-dichloro-benzyl)-2H-pyrazole-3-carboxylic acid phenylamide | 17 | 10 |
| 5-tert-Butyl-2-(2,4-dichloro-benzyl)-2H-pyrazole-3-carboxylic acid benzylamide | 18 | 9 |
| 1-(4-Chloro-phenyl)-5-phenyl-1H-pyrazole-3-carboxylic acid (4-dimethylamino-phenyl)-amide | 19 | 5 |
| 1-(4-Chloro-phenyl)-5-phenyl-1H-pyrazole-3-carboxylic acid (4-tert-butyl-phenyl)-amide | 20 | 20 |

TABLE 1-continued

| Compound | Example No | Guanidine Flux |
|---|---|---|
| 2-tert-Butyl-5-methyl-2H-pyrazole-3-carboxylic acid (4-tert-butyl-phenyl)-amide | 21 | <9 |
| 2-tert-Butyl-5-methyl-2H-pyrazole-3-carboxylic acid (3,4-dichloro-phenyl)-amide | 22 | <9 |
| 5-tert-Butyl-2-methyl-2H-pyrazole-3-carboxylic acid (3,4-dichloro-phenyl)-amide | 23 | <9 |
| 2-Benzyl-5-tert-butyl-2H-pyrazole-3-carboxylic acid (3,4-dichloro-phenyl)-amide | 24 | <9 |
| 2-Benzyl-5-tert-butyl-2H-pyrazole-3-carboxylic acid (4-tert-butylphenyl)-amide | 25 | 18 |
| 5-tert-Butyl-2-methyl-2H-pyrazole-3-carboxylic acid (4-tert-butyl-phenyl)-amide | 26 | <9 |
| 2-Benzyl-5-tert-butyl-2H-pyrazole-3-carboxylic acid (4-dimethylamino-phenyl)-amide | 27 | <9 |
| 2-Benzyl-5-tert-butyl-2H-pyrazole-3-carboxylic acid (3-oxazol-5-yl-phenyl)-amide | 28 | <9 |
| 5-tert-Butyl-2-methyl-2H-pyrazole-3-carboxylic acid (3-oxazol-5-yl-phenyl)-amide | 29 | 9 |
| 1-(4-Chloro-phenyl)-5-phenyl-1H-pyrazole-3-carboxylic acid (5-tert-butyl-isoxazol-3-yl)-amide | 30 | 15 |
| 2-tert-Butyl-5-methyl-2H-pyrazole-3-carboxylic acid (4-phenylcarbamoyl-phenyl)-amide | 31 | 22 |
| 2-Benzyl-5-tert-butyl-2H-pyrazole-3-carboxylic acid (3-phenylcarbamoyl-phenyl)-amide | 32 | 22 |
| 5-tert-Butyl-2-methyl-2H-pyrazole-3-carboxylic acid (3-phenylcarbamoyl-phenyl)-amide | 33 | 22 |
| 2-Benzyl-5-tert-butyl-2H-pyrazole-3-carboxylic acid (6-chloro-pyridin-3-yl)-amide | 34 | <9 |
| 1-tert-Butyl-5-methyl-1H-pyrazole-3-carboxylic acid (6-chloro-pyridin-3-yl)-amide | 35 | 5 |
| 1-tert-Butyl-5-methyl-1H-pyrazole-3-carboxylic acid (4-acetylamino-phenyl)-amide | 36 | 23 |
| 1-tert-Butyl-5-methyl-1H-pyrazole-3-carboxylic acid (3-benzyloxy-pyridin-2-yl)-amide | 37 | <9 |
| 5-Methyl-1-(4-methyl-benzyl)-1H-pyrazole-3-carboxylic acid (4-acetylamino-phenyl)-amide | 38 | 14 |
| 5-tert-Butyl-2-(2,4-dichloro-benzyl)-2H-pyrazole-3-carboxylic acid (4-acetylamino-phenyl)-amide | 39 | 24 |
| 2-Ethyl-5-thiophen-2-yl-2H-pyrazole-3-carboxylic acid (4-acetylamino-phenyl)-amide | 40 | <9 |
| 5-tert-Butyl-2-(2,4-dichloro-benzyl)-2H-pyrazole-3-carboxylic acid (4-(pyridin-3-yl) thiazol-2-yl)-amide | 41 | 14 |
| 2-Ethyl-5-thiophen-2-yl-2H-pyrazole-3-carboxylic acid (4-(pyridin-3-yl) thiazol-2-yl)-amide. | 42 | <9 |
| 2-Benzyl-5-tert-butyl-2H-pyrazole-3-carboxylic acid (4-acetylamino-phenyl)-amide | 43 | 16 |
| 5-tert-Butyl-2-methyl-2H-pyrazole-3-carboxylic acid (4-(pyridin-3-yl) thiazol-2-yl)-amide. | 44 | <9 |
| 5-tert-Butyl-2-methyl-2H-pyrazole-3-carboxylic acid [3-(4-methoxy-benzyl)-[1,2,4]oxadiazol-5-yl]-amide | 45 | 19 |
| 3-(Benzylthio)-5-(1-ethyl-3-methyl-1H-pyrazol-5-yl)-4-phenyl-4H-1,2,4-triazolehemihydrate | | 20 |
| 5-[3-(tert-Butyl)-1-(3-methylbenzyl)pyrazol-5-yl]-4-cyclohexyl-1,2,4-triazole-3-thiol | | <9 |
| 5-[3-tert-Butyl-1-(2,4-dichlorobenzyl)pyrazol-5-yl]-4-methyltriazole-3-thiol | | <9 |
| Ethyl 2-([5-[3-(tert-butyl)-1-(3-methylbenzyl)-1H-pyrazol-5-yl]-4-cyclohexyl-4H-1,2,4-triazol-3-yl]thio)acetate | | <9 |
| 3-[3-(tert-Butyl)-1-(2,4-dichlorobenzyl)-1H-pyrazol-5-yl]-4-phenyl-5-(prop-2-ynylthio)-4H-1,2,4-tziazole | | 18 |
| 3-Benzylsulfanyl-5-[5-tert-butyl-2-(4-fluoro-benzyl)-2H-pyrazol-3-yl]-4-methyl-4H-[1,2,4]triazole | | 12 |
| 2-Benzyl-5-tert-butyl-2H-pyrazole-3-carboxylic acid p-tolylamide | | 2 |
| 2-Benzyl-5-tert-butyl-2H-pyrazole-3-carboxylic acid (4-bromo-3-chloro-phenyl)-amide | | 3 |
| 1-tert-Butyl-5-methyl-1H-pyrazole-3-carboxylic acid (4-tert-butyl-phenyl)-amide | | 6 |
| 5-tert-Butyl-2-methyl-2H-pyrazole-3-carboxylic acid (4-chloro-phenyl)-amide | | 6 |
| 5-tert-Butyl-2-methyl-2H-pyrazole-3-carboxylic acid (4-tert-butyl-phenyl)-amide | | 2 |
| 5-Methyl-2-(4-methyl-benzyl)-2H-pyrazole-3-carboxylic acid (3-trifluoromethyl-phenyl)-amide | | 6 |
| 5-Methyl-1-(4-methyl-benzyl)-1H-pyrazole-3-carboxylic acid phenylamide | | 23 |
| 1-(2,6-Dichloro-benzyl)-5-methyl-1H-pyrazole-3-carboxylic acid m-tolylamide | | 7 |
| 2-{5-[5-tert-Butyl-2-(4-fluoro-benzyl)-2H-pyrazol-3-yl]-4-methyl-4H-[1,2,4]triazol-3-ylsulfanyl}-1-phenyl-ethanone | | 19.5 |
| 1-{5-[5-tert-Butyl-2-(4-fluoro-benzyl)-2H-pyrazol-3-yl]-4-methyl-4H-[1,2,4]triazol-3-ylsulfanyl}-3,3-dimethyl-butan-2-one | | 13 |
| 2-Benzyl-5-tert-butyl-2H-pyrazole-3-carboxylic arid N'-(3-trifluoromethylphenylcarbamoyl)hydrazide | | 0.5 |

EXAMPLE 54

The neuroprotective effect of the compounds of the invention on the optic nerve was assessed as follows.

Methods

Optic Nerve Pathology.

Optic nerves were excised from adult Wistar rats (weighing 240-280 g) after decapitation. They comprised lengths of nerve (each about 9 mm long) running from immediately behind the eyeball to just in front of the optic chiasm. The nerves were incubated in Erlenmeyer flasks (50 ml capacity) containing 20 ml of an artificial CSF (aCSF) solution composed of (mM): NaCl (120) KCl (2.0), $CaCl_2$ (2.0), $NaHCO_3$ (26), $KH_2PO_4$ (1.18), $MgSO_4$ (1.19) and glucose (11), continuously gassed with 95% $O_2$/5% $CO_2$. The flasks were held in a shaking water bath at 37° C.

After 1-2 h preincubation in aCSF, test nerves received the NO donor, PAPA/NO (1 mM) for 2 h or OGD was imposed by transferring the nerves for 1 h into aCSF lacking glucose and gassed with 5% $CO_2$ in $N_2$. Afterwards, the nerves were allowed a 90 min recovery period in aCSF. Putative protectant drugs were present from 15 min before until 15 min after the NO exposure or OGD.

The nerves were then fixed for 2 h in a mixture of 4% paraformaldehyde and 2.5% glutaraldehyde in 0.1 M phosphate buffer (pH 7.4), and post-fixed with 1% osmium tetroxide for 1 h. After dehydration the tissues were embedded in Durcupan resin. Semithin (1 μm) sections were stained with either toluidine blue.

To quantify the extent of axonal pathology under the light microscope, the degree of distension of the axon profiles was measured using an image analysis system as described previously (Garthwaite et al., (1999), *Neuroscience*, 94, 1219-1230). The data are expressed as mean number of axons greater than 2.5 μm in diameter per $10^4 m^2$ (±S.E.M.) in fields from 5-39 nerves.

Guanidium Ion Influx Assay

Results

1. Protection of Optic Nerve

Histological examination showed that NO caused extensive axonal degeneration. Quantitative morphometry of the index of axonopathy (the density of axons of diameter greater than 2.5 μm) indicated a 10-fold increase over control nerves (Table 2). The pathology was eliminated by the classical sodium channel blocker, tetrodotoxin, and by BW619C$_{89}$, a neuroprotective sodium channel inhibitor. A compound of the invention (3-(5'-hydroxymethyl-2-furyl)1-benzylindazole) was as effective as both these other agents.

Tests were also carried out to determine if the compound of the invention could also protect against axonal damage caused by severe oxygen- and glucose-deprivation (OGD). As indicated in Table 2, this procedure resulted in an index of axonopathy somewhat greater than that induced by NO and both BW619C$_{89}$ and the compound of the invention were able to protect to an equivalent degree.

TABLE 2

| Treatment | Index of Axonopathy | n |
|---|---|---|
| None | 23 ± 3 | 9 |
| PAPA/NO (1 mM) | 226 ± 22 | 10 |
| +Tetrodotoxin (1 µM) | 17 ± 4 | 4 |
| +BW619C89 (100 µM) | 26 ± 3 | 4 |
| +compound of invention (30 µM) | 24 ± 4 | 7 |
| OGD | 260 ± 6 | 4 |
| +BW619C89 (100 µM) | 53 ± 5 | 3 |
| +compound of invention | 72 ± 15 | 3 |

EXAMPLE 55

A further assay was conducted to assess the neuroprotective effect of the compounds of the invention on the optic nerve as follows.

Preparation

Nerves were excised from male Wistar rats (weighing 300-350 g) after sacrifice by $CO_2$ and decapitation. Each pair of nerves were transferred to 20 ml artificial CSF (aCSF) at 10° C.:

120 mM NaCl, 2 mM KCl, 2mM $CaCl_2$, 26 mM $NaHCO_3$, 1.18mM $KH_2PO_4$, 1.19 $MgSO_4$, 11 mM glucose, then gassed with 95% $O_2$/5% $CO_2$ in a shaking water bath at 37° C.

Once all nerves were excised, they were randomized (2 nerves per flask) and left to incubate for approx. 1 hr.

Oxygen and Glucose Deprivation

After incubation, relevant concentrations of compounds were added and gassing was continued for a further 15 minutes. OGD was then introduced by transferring the nerves into aCSF lacking glucose (+compound) and gassing with 5%$CO_2$ in $N_2$ for 1 hr. Control nerves (plus control+drug) were transferred to normal aCSF and gassed with $O_2$/$CO_2$ for the same interval. All nerves were then re-introduced to $OCO_2$ gassing and normal aCSF (+compound). After 15 minutes the nerves were transferred to normal aCSF (−compound) for a further 75 minutes.

A sufficient amount of aCSF was warmed and IBMX (22 mg/100 ml) was added and left to dissolve (approx. 1 hr).

Cyclic GMP Accumulation

The neuroprotective effect of the compounds of the invention was determined by establishing the amount of cGMP accumulation in the nerves. To to this, all nerves were transferred to aCSF containing IBMX for 10 minutes. After this time they were then exposed to 100 µM DEA/NO for 5 mins then inactivated in 200 µl boiling hypotonic buffer. Protein and cGMP contents were then measured Example:

| Flask | Title | ±OGD | Amount of compound (dissolved in DMSO) | [DEA/ NO] |
|---|---|---|---|---|
| 1 | Control | − | — | 100 µM |
| 2 | OGD | + | — | 100 µM |
| 3 | OGD + 1 µM cmpd | + | 20 µl 1 mM compound | 100 µM |
| 4 | OGD + 3 µM cmpd | + | 20 µl 3 mM compound | 100 µM |
| 5 | OGD + 10 µM cmpd | + | 20 µl 10 mM compound | 100 µM |
| 6 | OGD + 30 µM cmpd | + | 20 µl 30 mM compound | 100 µM |
| 7 | OGD + 100 µM cmpd | + | 20 µl 100 mM compound | 100 µM |
| 8 | OGD + 1 µM TTX | + | 20 µl 1 mM TTX citrate | 100 µM | results

The Table below sets out the results achieved with 30 µM of each drug. Results are given in terms of the % protection achieved These were derived by comparing the protection achieved by each drug with that achieved by TTX. TTX would, of course, be expected to provide substantially complete protection against OGD insult in this assay, as it shuts down all sodium channel activity.

| Compound | % protection accorded |
|---|---|
| 2-Benzyl-5-tert-butyl-2H-pyrazole-3-carboxylic acid p-tolylamide | 66 |
| 1-tert-Butyl-5-methyl-1H-pyrazole-3-carboxylic acid (4-tert-butyl-phenyl)-amide | 39 |
| 5-tert-Butyl-2-methyl-2H-pyrazole-3-carboxylic acid (4-chloro-phenyl)-amide | 62 |
| 5-tert-Butyl-2-methyl-2H-pyrazole-3-carboxylic acid (4-tert-butyl-phenyl)-amide | 18 |
| 1-(2,6-Dichloro-benzyl)-5-methyl-1H-pyrazole-3-carboxylic acid m-tolylamide | 29 |
| 2-{5-[5-tert-Butyl-2-(4-fluoro-benzyl)-2H-pyrazol-3-yl]-4-methyl-4H-[1,2,4]triazol-3-ylsulfanyl}-1-phenyl-ethanone | 18 |
| 2-Benzyl-5-tert-butyl-2H-pyrazole-3-carboxylic acid N'-(3-chlorophenylcarbamoyl) hydrazide | 12 |
| 2-{5-[5-tert-Butyl-2-(4-fluoro-benzyl)-2H-pyrazol-3-yl]-4-methyl-4H-[1,2,4]triazol-3-ylsulfanyl}-1-(4-chloro-phenyl)-ethanone | 19 |
| 3-Benzylsulfanyl-5-[5-tert-butyl-2-(4-fluoro-benzyl)-2H-pyrazol-3-yl]-4-methyl-4H-[1,2,4]triazole | 72 |

The invention claimed is:

1. A method of alleviating normal tension glaucoma, multiple sclerosis, a motorneurone disease, stroke, spinal cord injury, Alzheimer's disease, Parkinson's disease or pain in a patient, which method comprises administering to said patient an effective amount of a compound of formula (I), or a pharmaceutically acceptable salt thereof,

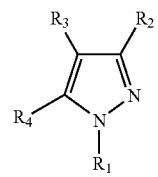

(I)

wherein:

R$_1$ is C$_1$-C$_6$ alkyl, C$_6$-C$_{10}$ aryl or —(C$_1$-C$_6$ alkyl)-(C$_6$-C$_{10}$ aryl);

R$_2$ is C$_6$-C$_{10}$ aryl, 5- to 10- membered heteroaryl, 3- to 6- membered heterocyclyl, C$_3$-C$_6$ carbocyclyl or —XR wherein X is a divalent C$_1$-C$_6$ alkyl, C$_2$-C$_6$ alkenyl or C$_2$-C$_6$ alkynyl group and R is C$_6$-C$_{10}$ aryl, 5- to 10- membered heteroaryl, 3- to 6-membered heterocyclyl or C$_3$-C$_6$ carbocyclyl, or R$_2$ is C$_1$-C$_6$ alkyl, C$_2$-C$_6$ alkenyl, C$_2$-C$_6$ alkynyl or —COR, —CONR'R'' or —CO$_2$R' wherein each R' and R'' is the same or different and is selected from hydrogen, C$_1$-C$_6$ alkyl, C$_6$-C$_{10}$ aryl and 5- to 10- membered heteroaryl and R is selected from C$_1$-C$_6$ alkyl, C$_6$-C$_{10}$ aryl and 5- to 10-membered heteroaryl; and either R$_3$ and R$_4$, together with the carbon atoms to which they are attached, form a phenyl group, or R$_3$ is hydrogen and R$_4$ is C$_1$- C$_6$ alkyl, C$_6$-C$_{10}$ aryl, 5- to 10- membered heteroaryl, —CONR'NR''COR, —CONR'—NR''CS—R, —CO$_2$R', —CONR'R'', —CONR'—NR''CO—NR'''R'''' or —CONR'—NR''CS—NR'''R'''', wherein each R is the same or different and is selected from C$_1$-C$_6$ alkyl, C$_6$-C$_{10}$ aryl, —(C$_1$-C$_6$ alkyl)-(C$_6$-C$_{10}$ aryl) and 5- to 10-membered heteroaryl and each R', R'', R''' and R'''' is the same or different and is selected from hydrogen, C$_1$-C$_6$ alkyl, C$_6$-C$_{10}$ aryl, —(C$_1$-C$_6$ alkyl)-(C$_6$-C$_{10}$ aryl) and 5- to 10- membered heteroaryl, said aryl and heteroaryl groups and moieties being unsubstituted or substituted by 1, 2 or 3 substituents selected from halogen, hydroxyl, —SH, C$_1$-C$_6$ alkyl, C$_2$-C$_6$ alkenyl, C$_2$-C$_6$ alkynyl, C$_6$-C$_{10}$ aryl, 5- to 10- membered heteroaryl, 3- to 6- membered heterocyclyl, C$_3$-C$_6$ carbocyclyl, —XY wherein X is a divalent C$_1$-C$_6$ alkyl, C$_2$-C$_6$ alkenyl or C$_2$-C$_6$ alkynyl group and Y is a C$_6$-C$_{10}$ aryl or 5- to 10- membered heteroaryl group, nitro, cyano, C$_1$-C$_6$ alkoxy, C$_2$-C$_6$ alkenyloxy, C$_2$-C$_6$ alkynyloxy, C$_1$-C$_6$ alkylthio, C$_2$-C$_6$ alkenylthio, C$_2$-C$_6$ alkynylthio, —OR, —SR, —COR', —CO$_2$R'', —CONR'''R'''', —NR'''R'''', —NR''—CO—R', —S—X—COR., —O—X—COR., —S—X—CO$_2$R., and —O—X—CO$_2$R., wherein R is C$_6$-C$_{10}$ aryl, 5- to 10- membered heteroaryl or —XY wherein X is a divalent C$_1$-C$_6$ alkyl, C$_2$-C$_6$ alkenyl or C$_2$-C$_6$ alkynyl group and Y is a C$_6$-C$_{10}$ aryl or 5- to 10- membered heteroaryl group, R' is selected from R, C$_1$-C$_6$ alkyl, C$_2$-C$_6$ alkenyl and C$_2$-C$_6$ alkynyl, R'' is selected from R' and hydrogen, R''' and R'''' are the same or different and are selected from R', hydrogen and hydroxy and R. is C$_1$-C$_6$ alkyl, C$_6$-C$_{10}$ aryl or 5- to 10- membered heteroaryl, the aryl, heteroaryl, carbocyclic and heterocyclic moieties in said substituents being unsubstituted or substituted by one or more further unsubstituted substituent selected from halogen, hydroxy, C$_1$-C$_6$ alkyl, C$_1$-C$_6$ haloalkyl, C$_1$-C$_6$ alkoxy, C$_1$-C$_6$ haloalkoxy and —NR'R'' wherein R' and R'' are the same or different and represent hydrogen or C$_1$-C$_6$ alkyl, said carbocyclic and heterocyclic groups being unsubstituted or substituted by up to 3 substituents selected from halogen, hydroxyl, —SH, C$_1$-C$_6$ alkyl, C$_2$-C$_6$ alkenyl, C$_2$-C$_6$ alkynyl, C$_6$-C$_{10}$ aryl, 5- to 10- membered heteroaryl, 3- to 6-membered heterocyclyl, C$_3$-C$_6$ carbocyclyl, nitro, cyano, C$_1$-C$_6$ alkoxy, C$_2$-C$_6$ alkenyloxy, C$_2$-C$_6$ alkynyloxy, C$_1$-C$_6$ alkylthio, C$_2$-C$_6$ alkenylthio, C$_2$-C$_6$ alkynylthio, —OR, —SR, —COR', —CO$_2$R'', —CONR'''R'''', —NR'''R'''', —S—X—COR. and —O—X—COR. wherein R is C$_6$-C$_{10}$ aryl, 5- to 10-membered heteroaryl or —XY wherein X is a divalent C$_1$-C$_6$ alkyl, C$_2$-C$_6$ alkenyl or C$_2$-C$_6$ alkynyl group and Y is a C$_6$-C$_{10}$ aryl or 5- to 10- membered heteroaryl group, R' is selected from R, C$_1$-C$_6$ alkyl, C$_2$-C$_6$ alkenyl and C$_2$-C$_6$ alkynyl, R'' is selected from R' and hydrogen, R''' and R'''' are the same or different and are selected from R', hydrogen and hydroxy and R. is C$_6$-C$_{10}$ aryl or 5- to 10- membered heteroaryl, the aryl, heteroaryl, carbocyclic and heterocyclic moieties in said substituent being unsubstituted or substituted by one or more further unsubstituted substituent selected from halogen, hydroxy, C$_1$-C$_6$ alkyl, C$_1$-C$_6$ haloalkyl, C$_1$-C$_6$ alkoxy, C$_1$-C$_6$ haloalkoxy and —NR'R'' wherein R' and R'' are the same or different and represent hydrogen or C$_1$-C$_6$ alkyl, said alkenyl and alkynyl groups or moieties being unsubstituted or substituted by 1 or 2 substituents selected from halogen, cyano, nitro, hydroxy, C$_1$-C$_6$ alkoxy and —NR'R'' substituents, wherein R' and R'' are the same or different and represent hydrogen or C$_1$-C$_6$ alkyl; and said alkyl groups and moieties being unsubstituted or substituted by 1 or 2 substituents selected from halogen, cyano, nitro, hydroxy, C$_1$-C$_6$ alkoxy and —NR'R'', wherein R' and R'' are the same or different and represent hydrogen or C$_1$-C$_6$ alkyl, or by 1, 2 or 3 halogen substituents.

2. A method according to claim 1, wherein:

said substituents on said aryl and heteroaryl groups and moieties are selected from halogen, —SH, hydroxy, C$_1$-C$_6$ alkyl, C$_6$-C$_{10}$ aryl, 5- to 10- membered heteroaryl, 3- to 6- membered heterocyclyl, C$_3$-C$_6$ carbocyclyl, —(C$_1$-C$_6$ alkyl)-(C$_6$-C$_{10}$ aryl), —(C$_1$-C$_6$ alkyl)-(5- to 10- membered heteroaryl), nitro, cyano, C$_1$-C$_6$ alkoxy, C$_2$-C$_6$ alkenyloxy, C$_2$-C$_6$ alkynyloxy, C$_1$-C$_6$ alkylthio, C$_2$-C$_6$ alkenylthio, C$_2$-C$_6$ alkynylthio, —OR, —SR, —COR', —CO$_2$R'', —CONR'''R'''', —NR'''R'''', —NR''—CO—R', —S—(C$_1$-C$_6$ alkyl)-CO—R. and —S—(C$_1$-C$_6$ alkyl)-CO$_2$R., wherein R is C$_6$-C$_{10}$ aryl or —(C$_1$-C$_6$ alkyl)-(C$_6$-C$_{10}$ aryl), R' is selected from R and C$_1$-C$_6$ alkyl, R'' is selected from R' and hydrogen, R''' and R'''' are the same or different and are selected from R', hydrogen and hydroxy, and R. is aryl or C$_1$-C$_6$ alkyl;

said substituents on said carbocyclic and heterocyclic groups and moieties are selected from halogen, —SH, hydroxy, C$_1$-C$_6$ alkyl, C$_6$-C$_{10}$ aryl, 5- to 10- membered heteroaryl, 3- to 6- membered heterocyclyl, C$_3$-C$_6$ carbocyclyl, nitro, cyano, C$_1$-C$_6$ alkoxy, C$_2$-C$_6$ alkenyloxy, C$_1$-C$_6$ alkylthio, C$_2$-C$_6$ alkenylthio, —OR, —SR, —COR', —CO$_2$R'', —CONR'''R'''', —NR'''R'''' and —S—(C$_1$-C$_6$ alkyl)-CO—R., wherein R is aryl or —(C$_1$-C$_6$ alkyl)-(C$_6$-C$_{10}$ aryl), R' is selected from R and C$_1$-C$_6$ alkyl, R'' is selected from R' and hydrogen, R''' and R'''' are the same or different and are selected from R', hydrogen and hydroxy, and R. is aryl or C$_1$-C$_6$ alkyl; and said substituents on said alkyl, alkenyl and alkynyl groups and moieties are selected from halogen, NMe$_2$, NHEt, NH$_2$ and OMe.

3. A method according to claim 1 wherein R$_1$ is C$_1$-C$_6$ alkyl, phenyl or benzyl.

4. A method according to claim 1, wherein R$_2$ is C$_6$-C$_{10}$ aryl, 5- to 10- membered heteroaryl, 3- to 6- membered heterocyclyl, C$_3$-C$_6$ carbocyclyl, C$_1$-C$_6$ alkyl, C$_2$-C$_6$ alkenyl, —CONR'R'' or —CO$_2$R' wherein R' and R'' are the same or different and are selected from hydrogen, $C_1$-$C_6$ alkyl, $C_6$-$C_{10}$ aryl and 5- to 10-membered heteroaryl.

5. A method according to claim 4, wherein $R_2$ is $C_6$-$C_{10}$ aryl, 5- to 10- membered heteroaryl, 3- to 6- membered heterocyclyl, $C_1$-$C_6$ alkyl or —CONR'R" wherein R' and R" are the same or different and are selected from hydrogen, $C_1$-$C_6$ alkyl, $C_6$-$C_{10}$ aryl and 5- to 10- membered heteroaryl.

6. A method according to claim 1, wherein $R_3$ is hydrogen.

7. A method according to any one of claims 1-6, wherein $R_4$ is $C_1$-$C_6$ alkyl, $C_6$-$C_{10}$ aryl, 5- to 10- membered heteroaryl, —CONR'—NR"COR, —CONR'—NR"CS—R, —$CO_2$R', —CONR'R", —CONR'—NR"CO—NR'''R"" or —CONR'—NR"CS—NR'''R"" wherein each R is the same or different and is selected from $C_1$-$C_6$ alkyl, $C_6$-$C_{10}$ aryl, —($C_1$-$C_6$ alkyl)-($C_6$-$C_{10}$ aryl) and 5- to 10- membered heteroaryl and each R', R", R''' and R–" is the same or different and is selected from hydrogen, $C_1$-$C_6$ alkyl, $C_6$-$C_{10}$ aryl, —($C_1$-$C_6$ alkyl)-($C_6$-$C_{10}$ aryl) and 5- to 10- membered heteroaryl.

8. A method according to claim 7, wherein $R_4$ is $C_1$-$C_6$ alkyl, 5- to 10- membered heteroaryl, —CONR'—NR"COR, —CONR'R", —CONR'—NR"CO—NR'''R"" or —CONR'—NR"CS—NR'''R""wherein R is $C_1$-$C_6$ alkyl or $C_6$-$C_{10}$ aryl and each R', R", R''' and R"" is the same or different and is selected from hydrogen, $C_1$-$C_6$ alkyl, $C_6$-$C_{10}$ aryl, —($C_1$-$C_6$ alkyl)-($C_6$-$C_{10}$ aryl) and 5- to 10- membered heteroaryl.

9. A method according to claim 1, wherein the compound of formula (I) is a compound of formula (Ia)

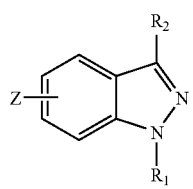

(Ia)

wherein $R_1$ and $R_2$ are as defined in claim 1 and Z is one or more selected from hydrogen, $C_1$-$C_6$ alkyl, halogen, hydroxy, $C_1$-$C_6$ alkoxy and —NR'R" wherein R' and R" are the same or different and are selected from hydrogen and $C_1$-$C_6$ alkyl.

10. A method according to claim 1, wherein the compound of formula (I) is a compound of formula (Ib)

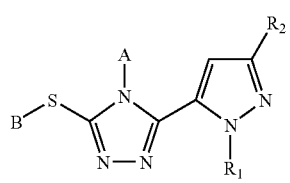

(Ib)

wherein:
$R_1$ and $R_2$ are as defined in claim 1;
A is hydrogen, $C_1$-$C_6$ alkyl, $C_2$-$C_6$ alkenyl, $C_6$-$C_{10}$ aryl, 5- to 10- membered heteroaryl, 3- to 6-membered heterocyclyl or $C_3$-$C_6$ carbocyclyl; and
B is hydrogen, $C_1$-$C_6$ alkyl, $C_2$-$C_6$ alkenyl, $C_1$-$C_6$ alkynyl, $C_6$-$C_{10}$ aryl, 5- to 10- membered heteroaryl, —XY wherein X is a divalent $C_1$-$C_6$ alkyl, $C_2$-$C_6$ alkenyl or $C_2$-$C_6$ alkynyl group and Y is a $C_6$-$C_{10}$ aryl or 5- to 10- membered heteroaryl group or —X'—COR or —X'—$CO_2$R wherein X' is a divalent $C_1$-$C_6$ alkyl, $C_2$-$C_6$ alkenyl or $C_2$-$C_6$ alkynyl group and R is $C_1$-$C_6$ alkyl, $C_6$-$C_{10}$ aryl or 5- to 10- membered heteroaryl.

11. A method according to claim 1, wherein the compound of formula (I) is a compound of formula (Ic)

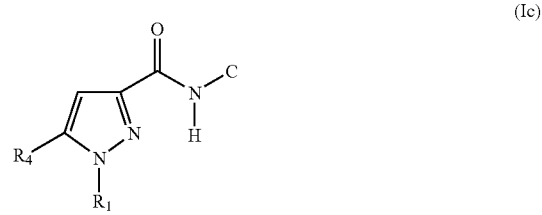

(Ic)

wherein:
$R_1$ and $R_4$ are as defined in claim 1; and
C is $C_6$-$C_{10}$ aryl, 5- to 10- membered heteroaryl, 3- to 6-membered heterocyclyl or $C_3$-$C_6$ carbocyclyl.

12. A method according to claim 1, wherein the compound of formula (I) is a compound of formula (Id)

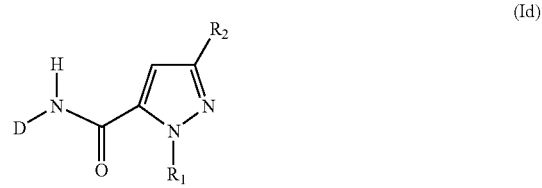

(Id)

wherein:
$R_1$ and $R_2$ are as defined in claim 1; and
D is $C_6$-$C_{10}$ aryl, 5- to 10- membered heteroaryl, —XY wherein X is a divalent $C_1$-$C_6$ alkyl group and Y is $C_6$-$C_{10}$ aryl, or D is —NR"CO—NR'''R"" wherein R" and R''' are the same or different and are hydrogen or $C_1$-$C_6$ alkyl and R"" is hydrogen, $C_1$-$C_6$ alkyl or $C_6$-$C_{10}$ aryl.

13. A method according to claim 1, wherein the compound of formula (I) or salt thereof is administered to alleviate pain.

14. A method according to claim 1, wherein the compound of formula (I) or salt thereof is administered to alleviate multiple sclerosis, spinal cord injury, or pain.

* * * * *